US011197731B2

(12) United States Patent
Hoffman et al.

(10) Patent No.: US 11,197,731 B2
(45) Date of Patent: Dec. 14, 2021

(54) AUXILIARY IMAGE DISPLAY AND MANIPULATION ON A COMPUTER DISPLAY IN A MEDICAL ROBOTIC SYSTEM

(71) Applicant: Intuitive Surgical Operations, Inc., Sunnyvale, CA (US)

(72) Inventors: Brian David Hoffman, Mountain View, CA (US); Rajesh Kumar, Sunnyvale, CA (US); David Q. Larkin, Menlo Park, CA (US); Nitish Swarup, Sunnyvale, CA (US); Guanghua G. Zhang, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 32 days.

(21) Appl. No.: 16/564,734

(22) Filed: Sep. 9, 2019

(65) Prior Publication Data

US 2019/0388169 A1 Dec. 26, 2019

Related U.S. Application Data

(60) Continuation of application No. 15/139,682, filed on Apr. 27, 2016, now abandoned, which is a division of (Continued)

(51) Int. Cl.

| | |
|---|---|
| ***A61B 34/37*** | (2016.01) |
| ***A61B 34/10*** | (2016.01) |

(Continued)

(52) U.S. Cl.

CPC .......... *A61B 34/37* (2016.02); *A61B 1/00193* (2013.01); *A61B 1/04* (2013.01);

(Continued)

(58) Field of Classification Search

CPC ......... A61B 34/37; A61B 34/10; A61B 34/70; A61B 34/71; A61B 34/76; A61B 90/36;

(Continued)

(56) References Cited

U.S. PATENT DOCUMENTS 5,182,728 A 1/1993 Shen et al.
5,279,309 A 1/1994 Taylor et al.

(Continued)

FOREIGN PATENT DOCUMENTS

EP 514584 A2 11/1992
JP 8111816 A 4/1996

(Continued)

OTHER PUBLICATIONS

IDL ("Working with Images in IDL", 2001) (Year: 2001).*

(Continued)

*Primary Examiner* — Xin Sheng

(74) *Attorney, Agent, or Firm* — Haynes and Boone, LLP

(57) ABSTRACT

A medical system may comprise a stereo display and an input device. The medical system may also comprise a processor configured to generate a three-dimensional image of an anatomical object and cause the three-dimensional image of the anatomical object and a two-dimensional window to be displayed. The processor may also be configured to cause a position and an orientation of the two-dimensional window relative to the three-dimensional image of the anatomical object to be changed on the stereo display by manipulation of the input device. The processor may also be configured to define a cut-plane to indicate a two-dimensional slice of the three-dimensional image of the anatomical object. The processor may also be configured to cause the two-dimensional slice of the three-dimensional image of the anatomical object to be displayed. An orientation of the displayed two-dimensional slice may be dif- (Continued)

ferent than an orientation of the cut-plane with the three-dimensional image.

20 Claims, 8 Drawing Sheets

Related U.S. Application Data application No. 11/583,963, filed on Oct. 19, 2006, now abandoned.

(60) Provisional application No. 60/728,450, filed on Oct. 20, 2005.

(51) Int. Cl.

| | |
|---|---|
| ***A61B 34/00*** | (2016.01) |
| ***A61B 90/00*** | (2016.01) |
| ***G06F 3/01*** | (2006.01) |
| ***G06F 3/0484*** | (2013.01) |
| ***G06F 3/0481*** | (2013.01) |
| ***G06F 3/0346*** | (2013.01) |
| ***G06F 3/0486*** | (2013.01) |
| ***A61B 1/00*** | (2006.01) |
| ***A61B 1/04*** | (2006.01) |
| ***A61B 1/313*** | (2006.01) |
| ***A61B 5/055*** | (2006.01) |
| ***A61B 5/00*** | (2006.01) |
| ***A61B 18/12*** | (2006.01) |
| ***A61B 90/10*** | (2016.01) |
| ***A61B 18/14*** | (2006.01) |
| ***A61B 34/30*** | (2016.01) |
| ***A61N 7/02*** | (2006.01) |
| ***A61B 18/00*** | (2006.01) |

(52) U.S. Cl.

CPC .............. *A61B 1/313* (2013.01); *A61B 5/055* (2013.01); *A61B 5/742* (2013.01); *A61B 18/12* (2013.01); *A61B 34/10* (2016.02); *A61B 34/70* (2016.02); *A61B 34/71* (2016.02); *A61B 34/76* (2016.02); *A61B 90/36* (2016.02); *G06F 3/011* (2013.01); *G06F 3/016* (2013.01); *G06F 3/0346* (2013.01); *G06F 3/0481* (2013.01); *G06F 3/0486* (2013.01); *G06F 3/04817* (2013.01); *G06F 3/04842* (2013.01); *G06F 3/04845* (2013.01); *G06F 3/04847* (2013.01); *A61B 18/1482* (2013.01); *A61B 34/30* (2016.02); *A61B 90/361* (2016.02); *A61B 90/37* (2016.02); *A61B 2018/00577* (2013.01); *A61B 2018/00595* (2013.01); *A61B 2018/00982* (2013.01); *A61B 2018/00994* (2013.01); *A61B 2090/101* (2016.02); *A61B 2090/364* (2016.02); *A61B 2090/374* (2016.02); *A61B 2090/378* (2016.02); *A61B 2090/3782* (2016.02); *A61N 7/022* (2013.01); *G06F 2203/014* (2013.01); *G06F 2203/04804* (2013.01); *G06F 2203/04806* (2013.01)

(58) Field of Classification Search

CPC ....... A61B 1/00193; A61B 1/04; A61B 1/313; A61B 5/055; A61B 5/742; A61B 18/12; A61B 34/30; A61B 2090/101; A61B 90/361; A61B 2090/364; A61B 90/37; A61B 2090/374; A61B 2090/378; A61B 2090/3782; A61B 18/1482; A61B 2018/00577; A61B 2018/00595; A61B 2018/00982; A61B 2018/00994; G06F 3/011; G06F 3/016; G06F 3/0346; G06F 3/0481; G06F 3/04817; G06F 3/04842; G06F 3/04845; G06F 3/04847; G06F 3/0486; G06F 2203/014; G06F 2203/04804; G06F 2203/04806; A61N 7/022

See application file for complete search history.

(56) References Cited

U.S. PATENT DOCUMENTS

| | | | | |
|---|---|---|---|---|
| 5,397,323 | A | 3/1995 | Taylor et al. | |
| 5,417,210 | A * | 5/1995 | Funda ................ | A61B 1/00193 348/65 |
| 5,493,595 | A | 2/1996 | Schoolman | |
| 5,551,432 | A | 9/1996 | Iezzi | |
| 5,572,999 | A | 11/1996 | Funda et al. | |
| 5,749,362 | A | 5/1998 | Funda et al. | |
| 5,759,153 | A | 6/1998 | Webler et al. | |
| 5,765,561 | A | 6/1998 | Chen et al. | |
| 5,788,688 | A | 8/1998 | Bauer et al. | |
| 5,797,849 | A | 8/1998 | Vesely et al. | |
| 5,810,008 | A | 9/1998 | Dekel et al. | |
| 5,817,022 | A | 10/1998 | Vesely | |
| 5,836,880 | A | 11/1998 | Pratt | |
| 5,842,473 | A | 12/1998 | Fenster et al. | |
| 5,842,993 | A | 12/1998 | Eichelberger et al. | |
| 5,853,367 | A | 12/1998 | Chalek et al. | |
| 5,887,121 | A | 3/1999 | Funda et al. | |
| 6,129,670 | A | 10/2000 | Burdette et al. | |
| 6,201,984 | B1 | 3/2001 | Funda et al. | |
| 6,241,725 | B1 | 6/2001 | Cosman | |
| 6,256,529 | B1 | 7/2001 | Holupka et al. | |
| 6,312,391 | B1 | 11/2001 | Ramadhyani et al. | |
| 6,402,737 | B1 | 6/2002 | Tajima et al. | |
| 6,522,906 | B1 * | 2/2003 | Salisbury, Jr. ......... | A61B 1/313 600/102 |
| 6,599,247 | B1 | 7/2003 | Stetten | |
| 6,602,185 | B1 | 8/2003 | Uchikubo | |
| 6,642,836 | B1 | 11/2003 | Wang et al. | |
| 6,799,065 | B1 | 9/2004 | Niemeyer | |
| 6,837,883 | B2 | 1/2005 | Moll et al. | |
| 7,107,124 | B2 | 9/2006 | Green | |
| 7,413,565 | B2 | 8/2008 | Wang et al. | |
| 2002/0193800 | A1 | 12/2002 | Kienzle, III | |
| 2003/0055410 | A1 | 3/2003 | Evans et al. | |
| 2004/0106916 | A1 | 6/2004 | Quaid et al. | |
| 2004/0111183 | A1 | 6/2004 | Sutherland et al. | |
| 2005/0065658 | A1 | 3/2005 | Green | |
| 2005/0203375 | A1 | 9/2005 | Willis et al. | |
| 2006/0058988 | A1 | 3/2006 | Defranoux et al. | |
| 2006/0112334 | A1 | 5/2006 | Endrikhovski et al. | |
| 2008/0020362 | A1 | 1/2008 | Cotin et al. | |
| 2008/0033240 | A1 | 2/2008 | Hoffman et al. | |

FOREIGN PATENT DOCUMENTS

| | | | |
|---|---|---|---|
| JP | 9173352 | A | 7/1997 |
| JP | 10322629 | A | 12/1998 |
| WO | WO-9424631 | A1 | 10/1994 |
| WO | WO-2007030173 | A1 | 3/2007 |
| WO | WO-2007047782 | A2 | 4/2007 |

OTHER PUBLICATIONS

Font, Iciar, et al. “Haptic feedback designs in teleoperation systems for minimal invasive surgery.” 2004 IEEE International Conference on Systems, Man and Cybernetics (IEEE Cat. No. 04CH37583). vol. 3. IEEE, 2004. (Year: 2004).*

3D Slicer, http://slicer.org/welcome.html, downloaded Oct. 25, 2006, p. 1; and Introduction, http:/slicer.org/intro/index.html, downloaded Oct. 25, 2006, pp. 1-4.

Abolmaesumi, Purang et al., “A User Interface for Robot-Assisted Diagnostic Ultrasound,” IEEE Robotics and Automation Conference, 2001, pp. 1549-1554, vol. 2, IEEE.

(56) References Cited

OTHER PUBLICATIONS

Abolmaesumi, Purang et al., "Image Guided Control of a Robot for Medical Ultrasound," IEEE Transactions on Robotics and Automation, 2002, pp. 11-23, vol. 18—Issue 1, IEEE.
Ahlering, Thomas. E. et al., "Robotic radical prostatectomy: a technique to reduce pT2 positive margins," Urology, 2004, pp. 1224-1228, vol. 64 Issue 6, Elsevier Inc.
Azuma, Ronald T., "A Survey of Augmented Reality," Teleoperators and Virtual Environments, 1997, pp. 355-385, vol. 6—No. 4.
Bajura M., et al., "Merging Virtual Objects with the Real World: Seeing Ultrasound Imagery within the Patient," in: Computer-Integrated Surgery, R.H. Taylor, et al., Eds., Cambridge, Mass.: MIT Press, 1996, pp. 245-254.
Banovac, Filip et al., "Liver Tumor Biopsy in a Respiring Phantom with the Assistance of a Novel Electromagnetic Navigation Device," 2002, pp. 200-207, Springer-Verlag.
Bartels, Richard H. et al., "An Introduction to Splines for use in Computer Graphics and Geometric Modeling," 1987, 6 Pages total , Morgan kaufmann publishers, INC.
Bartels, Richard H. et al., "Solution of the Matrix Equation AX+XB=C," Communications of the ACM, 1972, pp. 820-826, vol. 15—Issue 9, ACM Press.
Berkelman, Peter J. et al., "A Compact Compliant Laparoscopic Endoscope Manipulator," IEEE International Conference on Robotics and Automation, 2002, pp. 1870-1875, vol. 2, IEEE.
Berkelman, Peter J. et al., "A miniature Instrument Tip Force Sensor for Robot/Human Cooperative Micro surgical Manipulation with Enhanced Force Feedback," Proceedings of the Third International Conference on Medical Image Computing and Computer-Assisted Intervention, Springer-Verlag, 2000, pp. 897-906, vol. 1935.
Berkelman, Peter J. et al., "A miniature microsurgical instrument tip force sensor for enhanced force feedback during robot-assisted manipulation," IEEE Transactions on Robotics and Automation, 2000, pp. 917-922, vol. 19—Issue 5, IEEE.
Berkelman, Peter J. et al., "Performance Evaluation of a Cooperative Manipulation Microsurgical Assistant Robot Applied to Stapedotomy," Medical Image Computing and Computer-Assisted Interventions, Lecture Notes in Computer Science, 2001, pp. 1426-1429, vol. 2208.
Bettini, A. et al., "Vision Assisted Control for Manipulation Using Virtual Fixtures," IEEE/RSJ International Conference on Intelligent Robots and Systems (IROS), Oct. 29-Nov. 3, 2001, pp. 1171-1176, vol. 2.
Bettini, A. et al., "Vision Assisted Control for Manipulation Using Virtual Fixtures: Experiments at Macro and Micro Scales," IEEE Conference on Robots and Automation (ICRA '02), May 11-15, 2002, pp. 3354-3361, vol. 4, IEEE.
Bettini, Alessandro et al., "Vision Assisted Control for Manipulation Using Virtual Fixtures," IEEE Transactions on Robotics, 2004, pp. 953-966, vol. 20—Issue 6, IEEE.
Boctor, Emad et al., "A Novel Closed Form Solution for Ultrasound Calibration," IEEE International Symposium on Biomedical Imaging (ISBI), Arlington, VA, vol. 1, pp. 527-530, Apr. 15-18, 2004.
Boctor, Emad, M. et al., "A dual-armed robotic system for intraoperative ultrasound guided hepatic ablative therapy: a prospective study," Proc of IEEE 2004 International Conference on Robotics & Automation, 2004, pp. 2517-2522, vol. 3, IEEE.
Boctor, Emad, M. et al., "A Rapid calibration method for registration and 3D tracking of ultrasound images using spatial localizer," Ultrasonic Imaging and Signal Processing, 2003, pp. 521-532, vol. 5035, SPIE.
Boctor, Emad, M. et al., "CISUS: An integrated 3D ultrasound system for IGT using a modular tracking API," Proceedings of the SPIE, 2004, pp. 247-256, vol. 5367, SPIE.
Boctor, Emad, M. et al., "Development of a Robotically-Assisted 3-D Ultrasound System for Radiofrequency Ablation of Liver Tumors," 6th World Congress of the Hepato-Pancreato-Biliary Association, Abstract No. 167, 2004, p. 46, vol. 6—Supplement 1, Taylor & Francis Health Science.
Boctor, Emad, M. et al., "PC Based system for calibration, Reconstruction Processing and Visualization of 3D Ultrasound Data Based on a Magnetic-Field Position and Orientation Sensing System," Proceedings of the International Conference on Computational Science—Part II, Lecture Notes in Computer Science , 2001, pp. 13-22, vol. 2074, Springer.
Boctor, Emad, M. et al., "Robot-assisted 3D strain imaging for monitoring thermal ablation of liver," Annual congress of the Society of American Gastrointestinal Endoscopic Surgeons (SAGES),Emerging Technology Lunch Poster TP004, 2005, pp. 240-241.
Boctor, Emad, M. et al., "Robotic Strain Imaging for Monitoring Thermal Ablation of Liver," Medical Image Computing and Computer-Assisted Intervention MICCAI, 2004, pp. 81-88, vol. 2, Springer-Verlag.
Boctor, Emad, M. et al., "Robotically assisted intraoperative ultrasound with application to ablative therapy of liver cancer," Medical Imaging:Visualization, Image Guided Procedures, and Display, 2003, pp. 281-291, vol. 5029, SPIE.
Boctor, Emad, M. et al., "Tracked 3D ultrasound in radio-frequency liver ablation," in Medical Imaging 2003:Ultrasonic Imaging and Signal Processing, 2003, pp. 174-182, vol. 5035, SPIE.
Boudet,Sylvie et al., "An Integrated Robotics and Medical Control Device to Quantify Atheromatous Plaques: Experiments on the Arteries of a Patient," Proc of IEE/RSH International Conference on Intelligent Robots and Systems, 1997, pp. 1533-1538, vol. 3.
Brown, Myron M. et al., "Advances in Computational Stereo," IEEE Transactions on Pattern Analysis and Machine Intelligence (PAMI), 2003, pp. 993-1008, vol. 25 Issue, IEEE.
Burschka, Darius et al., "Navigating Inner Space: 3-D Assistance for Minimally Invasive Surgery," Robotics and Autonomous Systems, 2005, pp. 5-26, vol. 52—Issue 1, Elsevier.
Burschka, Darius et al., "Principle and Practice of Real-Time Visual Tracking for Navigation and Mapping," IEEE Workshop on Robotic Sensing: Robotics in the Automotive Industry, 2004, pp. 1-8, IEEE.
Burschka, Darius et al., "Scale-Invariant Registration of Monocular Endoscopic Images to CT-Scans for Sinus Surgery," Med Image Anal, 2004, pp. 413-421, vol. 2, Springer-Verlag.
Burschka, Darius et al., "Scale-Invariant Registration of Monocular Stereo Images to 3D Surface Models," IEEE Int. Conf. on Robots and Systems, 2004, pp. 2581-2586, vol. 3, IEEE.
Bzostek, Andrew et al., "A Testbed System for Robotically Assisted Percutaneous Pattern Therapy," Medical Image Computing and Computer-Assisted Surgery, Lecture Notes In Computer Science, 1999, pp. 1098-1107, vol. 1679, Springer.
Bzostek, Andrew et al., "An automated system for precise percutaneous access of the renal collecting system," Proceedings of the First Joint Conference on Computer Vision, Virtual Reality and Robotics in Medicine and Medial Robotics and Computer-Assisted Surgery, Lecture Notes In Computer Science, 1997, pp. 299-308, vol. 1205, Springer-Verlag.
Bzostek, Andrew, "Image Guided Percutaneous Pattern Placement in Soft Tissue," The Johns Hopkins University Dept. of Computer Science: Baltimore, 1997, pp. 2007-01-22.
Cadeddu, Jeffrey A. et al., "A Robotic System for Percutaneous Renal Access," The Journal of Urology, 1997, pp. 1589-1593, vol. 158—Issue 4.
Cadeddu, Jeffrey et al., "A robotic system for percutaneous renal access incorporating a remote center of motion design," Journal of Endourolog, 1998, S237, vol. 12.
Cannon, Jeremy W. et al., "Real-time three-dimensional ultrasound for guiding surgical tasks," Computer Aided Surgery, 2003, pp. 82-90, vol. 8—No. 2, John Wiley & Sons.
Carr, J., "Surface reconstruction in 3D medical imaging," PhD Thesis, Part 1, University of Canterbury, Christchurch, New Zealand, 1996, 112 Pages.
Carr, J., "Surface reconstruction in 3D medical imaging," PhD Thesis, Part 2, University of Canterbury, Christchurch, New Zealand, 1996, 112 Pages.
Cash, David M. et al., "Incorporation of a laser range scanner into an image-guided surgical system," The International Society for Optical Engineering (SPIE), Medical Imaging 2003: Visualization,

(56) References Cited

OTHER PUBLICATIONS

Image-Guided Procedures, and Display; San Diego, CA, Ed. Robert L. Galloway, 2003, pp. 269-280, vol. 5029.
Chang, Jun Keun et al., "Intravascular micro active catheter for minimal invasive surgery," 1st Annual International Conference on Microtechnologies in Medicine and Biology, 2000, pp. 243-246.
Chen, Homer H. "A Screw Motion Approach to Uniqueness Analysis of Head-Eye Geometry," Computer Vision and Pattern Recognition, 1991, pp. 145-151, IEEE.
Chinzei, Kiyoyuki et al., "MR Compatible Surgical Assist Robot: System Integration and Preliminary Feasibility Study," in Proceedings of Third International Conference On Medical Imaging and Computer Assisted Surgery (MICCAI), 2000, pp. 921-930, vol. 1935, Springer-Verlag.
Choti, Michael A. et al., "Trends in Long Term Survival Following Liver Resection for Hepatic Colorectal Metastases," Ana Surg, 2002, pp. 759-766, vol. 235—No. 6, Lippincott Williams & Wilkins.
Choti, Michael A., "Hepatic Radiofrequency Ablation," Cancer Journal, 2000, pp. S291-S292, vol. 6—issue 4, Jones and Bartlett.
Choti, Michael A., "Surgical Management of Hepatocellular Carcinoma: Resection and Ablation," Journal of Vascular and Interventional Radiology, 2002, pp. S197-S203, vol. 13—No. 9.
Chung, Mathew et al., "Laparascopic Radiofrequency Ablation of Unresectable Hepatic Malignancies," Surg Endosc, 2001, pp. 1020-1026, vol. 15—No. 9, Springer-Verlag.
Cleary, Kevin et al., "State of the art surgical robotics clinical applications and technology challenges," Computer Aided Surgery, 2001, pp. 312-328, vol. 6; Part 6, John Wiley & Sons.
Cleary,K. et al., "Robotically-assisted spine nerve blocks," Radiology, 2001, 1 page, vol. 221—No. 618.
D'Angelica M., "Staging Laparoscopy for Potentially Respectable Noncolorectal," Ann Surg Oncol, 2002, pp. 204-209, vol. 9—No. 2, Lippincott Williams & Wilkins.
Daniilidis, Konstantinos, Hand-Eye Calibration Using Dual Quaternions, Int. J. of Robotics Research, 1999, pp. 286-298, vol. 18 (3), Sage Publications, Inc.
Davies, Brain L. et al., "A Robotic system for tkr surgery," Proceedings of 3rd Annual North American Program on Computer Assisted Orthopaedic Surgery (CAOS USA), University of Pittsburgh Medical Center, Pittsburgh, Pennsylvania,published in Computer Aided Surgery, Jun. 17-19, 1999, p. 339, vol. 4—Iss. 6.
Davies, S.C., et al., "Ultrasound Quantitaion of Respiratory Organ Motion in the Upper Abdomen," British Journal of Radiology, Nov. 1994, vol. 67 (803), pp. 1096-1102.
De Cunha, D. et al., The MIDSTEP System for Ultrasound guided Remote Telesurgery, Proceedings of the 20th Annual International Conference of the IEEE Engineering in Medicine and Biology Society, 1998, pp. 1266-1269, vol. 3—No. 29, IEEE.
Degoulange, E. et al., "HIPPOCRATE: an intrinsically safe robot for medical applications," IEEE/RSH International Conference on Intelligent Biomedicine, 1998, pp. 959-964, vol. 2, IEEE.
Delgorge, Cecile et al., "A Tele-Operated Mobile Ultrasound Scanner Using a Light-Weight Robo," IEEE Transactions on Information Technology in Biomedicine, 2005, pp. 50-58, vol. 9 No. 1, IEEE.
Dewan, Maneesh et al., "Vision-Based Assistance for Ophthalmic Micro-Surgery," Proceedings of Seventh International Conference on Medical Image Computing and Computer-Assisted Intervention (MICCAI), 2004, pp. 49-57, vol. 3217, Springer-Verlag.
Dodds, Zachary et al., "A hierarchical architecture for vision-based robotic manipulation tasks," in Proceedings of the International Conference on Vision Systems, 1999, pp. 312-330, vol. 542, Springer-Verlag.
Doggett, Stephen W., "Image Registered Real Time Intra-Operative Treatment Planning: Permanent Seed Brachytherapy," 2000, p. 4.
Eldridge, B. et al., "A Remote Center of Motion Robotic Arm for Computer Assisted Surgery," Robotica, 1996, pp. 103-109, vol. 14 Issue 1.
Ellsmere, James et al., "A navigation system for augmenting laparoscopic ultrasound," Medical Image Computing and Computer-Assisted Intervention, Lecture Notes in Computer Science, 2003, pp. 184-191, Springer.
Fattal, Lischinsk, "Variational Classification for Visualization of 3D Ultrasound Data," Proceedings of the conference on Visualization, 2001, pp. 403-410, IEEE Computer Society.
Fenster, Aaron, et al., "3-D Ultrasound Imaging:A Review," IEEE Engineering and Medicine and Biology Magazine, Nov.-Dec. 1996, pp. 41-51, vol. 15—Issue 6, IEEE.
Fenster, Aaron, et al., "Three-dimensional ultrasound imaging of the prostate," SPIE International Symposium on Medical Imaging,San Diego, California,Published in SPIE: Medical Physics, Feb. 20-26, 1999, pp. 2-11, vol. 3859, SPIE.
Fichtinger, Gabor et al., "Robotically Assisted Percutaneous Local Therapy and Biopsy," 10th International Conference of Advance Robotics, 2001, pp. 133-151, IEEE.
Fichtinger, Gabor et al., "Surgical CAD/CAM and its application for robotically assisted percutaneous procedures," 30th Applied Imagery Pattern Recognition Workshop (AIPR), 2001, pp. 3-8, IEEE.
Fichtinger, Gabor et al., "System For Robotically Assisted Prostate Biopsy and Therapy With intraOperative CT Guidance," Journal of Academic Radiology, 2002, pp. 60-74, vol. 9 No. 1, Elsevier.
Fichtinger, Gabor et al., "Transrectal prostate biopsy inside closed MRI scanner with remote actuation under real-time image guidance," Medical Image Computing and Computer-Assisted Intervention, Lecture Notes in Computer Science, 2002, pp. 91-98, vol. 2488, Springer Verlag.
Frantz D.D et al., "Accuracy assessment protocols for electromagnetic tracking systems," Physics in Medicine and Biology, 2003, pp. 2241-2251, Issue 48.
Fuchs, Henry et al., "Augmented Reality Visualization for Laparoscopic Surgery," Medical Image Computing and Computer-Assisted Intervention, 1998, pp. 934-943, vol. 1496, Springer-Verlag.
Funda J., et al., "An experimental user interface for an interactive surgical robot," In 1st International Symposium on Medical Robotics and Computer Assisted Surgery (MRCAS 94), 1994, pp. 196-203.
Funda J., et al., "Constrained Cartesian Motion Control for Teleoperated Surgical Robots," IEEE Transactions on Robotics and Automation, IEEE, Jun. 1996, vol. 12 (3), pp. 453-465.
Funda, Janez et al., "Comparison of two manipulator designs for laparoscopic surgery," SPIE International Symposium on Optical Tools for Manufacturing and Advanced Automation, 1994, pp. 172-183, vol. 2351, Telemanipulator and Telepresence Technologies.
Funda, Janez et al., "Control and evaluation of a 7-axis surgical robot for laparoscopy," IEEE Int. Conf. on Robotics and Automation, 1995, pp. 1477-1484, vol. 2, IEEE.
Funda, Janez et al., "Image-Guided Command and Control of a Surgical Robot," Proc. Medicine Meets Virtual Reality II, 1994, pp. 52-57.
Funda, Janez et al., "Optimal Motion Control for Teleoperated Surgical Robots," Intl. Symp. on Optical Tools for Manuf. & Adv Autom,Telemanipulator Technology and Space Telerobotics, 1993, pp. 211-222, vol. 2057, SPIE.
Garrett, William F. et al., "Real-Time Incremental Visualization of Dynamic Ultrasound Volumes Using Parallel BSP Trees," IEEE Proceedings Visualization, 1996, pp. 235-240, 490, IEEE.
Gee, Andrew et al., "Processing and visualizing three-dimensional ultrasound data," Journal of Radiology, 2004, pp. 186-193, vol. 77.
Gelb, A., et al., Table of Contents for "Applied Optimal Estimation," The Analytic Science Corporation, MIT Press, Cambridge, Massachusetts,1974, 4 pages.
Gennari, G. et al., "Probabilistic data association methods in visual tracking of groups," IEEE Conference on Computer Vision and Pattern Recognition, 2004, pp. I-790-1-797, vol. 1—issue. 27, IEEE.
Gigot, Jean-Francois et al., "Laparoscopic Liver Resection for Malignant Liver Tumors Prclimary Results of a Multicenter European Study." Ann Surg, 2002, pp. 90-97, vol. 236—issue 1.

(56) References Cited

OTHER PUBLICATIONS

Gonzales, Adriana Vilchis et al., "A System for Robotic Tele-echography," Medical Image Computing and Computer-Assisted Intervention, 2001, pp. 326-334, vol. 2208, Springer.
Hager G., et al., "The X Vision System: A Portable Substrate for Real Time Vision Applications," Computer Vision and Image Understanding, 1998, vol. 69 (1),pp. 23-37.
Hager Gregory D. et al., "Multiple Kernel Tracking with SSD," Proceedings of the IEEE Conference on Computer Vision and Pattern Recognition (CVPR 2004), 2004, pp. I-790-I-797, vol. 1—issue 27, IEEE.
Hager, Gregory D. et al., "Efficient Region Tracking With Parametric Models of Geometry and Illumination," IEEE Transactions on Pattern Analysis and Machine Intelligence, 1998, pp. 1025-1039, vol. 20—issue. 10, IEEE.
Hager, Gregory D., "A Modular System for Robust Positioning Using Feedback from Stereo Vision," IEEE Transactions on Robotics and Automation, Aug. 1997, vol. 13 (4), pp. 582-595.
Hannaford, Blake et al., "Performance Evaluation of a Six-Axis Generalized Force-Reflecting Teleoperator," IEEE Transactions on Systems, Man, and Cybernetics, 1991, pp. 620-633, vol. 21—No. 3, IEEE.
Harris, S.J. et al., "Experiences with Robotic Systems for Knee Surgery," First Joint Conference of CVRMed and MRCAS. Mar. 19-22, 1997, Grenoble, France; Springer, 1997, pp. 757-766.
Herline A.J., et al., "Image-Guided Surgery: Preliminary Feasibility Studies of Frameless Stereotactic Liver Surgery," Archives of Surgery, 1999, vol. 134 (6), pp. 644-650.
Herline, Alan J. et al., "Surface Registration for Use in Interactive," Image-Guided Liver Surgery, Computer Aided Surgery, 2000, pp. 11-17, vol. 5—No. 2.
Hespanha J.P., et al., "What Tasks Can Be Performed with an Uncalibrated Stereo Vision System," International Journal of Computer Vision, Nov. 1999, vol. 35 (1), 33 pages.
Ho. S. C.et al., "Robot Assisted Knee Surgery," IEEE Engineering in Medicine and Biology Magazine, 1995, pp. 292-300, vol. 14—Iss. 3, IEEE.
Hong, Jae-Sung et al., "A Motion Adaptable Needle Placement Instrument Based on Tumor Specific Ultrasonic Image Segmentation," Fifth International Conference on Medical Image Computing and Computer Assisted Intervention, MICCAI '02, Tokyo, Japan, Jul. 2002, pp. 122-129.
Hutchinson, Seth et al., "A Tutorial Visual Servo Control," IEEE Transactions on Robotics and Automation, 1996, pp. 651-670, vol. 12 issue.5, IEEE.
Jain, Ameet Kumar et al., "Understanding Bone Responses in B-mode Ultrasound Images and Automatic Bone Surface Extraction using a BayesianProbabilistic Framework," SPIE Medical Imaging, 2004, pp. 131-142, vol. 5373.
Joskowicz L., et al., "Computers in Imaging and Guided Surgery," Computing in Science and Engineering, 2001, vol. 3 (5), pp. 65-72.
Jurie, Frederic et al., "Hyperplane Approximation for Template Matching," IEEE Transactions on Pattern Analysis and Machine Intelligence(PAMI), 2002, pp. 996-1000, vol. 24—Issue 7, IEEE.
Kane, Robert A., "Intraoperative Ultrasonography, History, Current State of the Art, and Future Directions," J Ultrasound Med, 2004, pp. 1407-1420, vol. 23.
Kaplan, Irving, "Minimizing Rectal and Urinary Complications in Prostate Brachytherapy," Journal of Endourology, 2000, pp. 381-383.
Kapoor A., et al., "Simple Biomanipulation Tasks with "Steady Hand" Cooperative Manipulator," Lecture Notes in Computer Science, 2003, vol. 2878, pp. 141-148.
Kapoor, Ankur et al., "Suturing in Confined Spaces: Constrained Motion Control of a Hybrid 8-DOF Robot," Proceedings, 12th International Conference on Advanced Robotics, 2005, pp. 452-459.
Kavoussi L.R., "Laparoscopic Donor Neptarectomy," Kidney International, 2000, vol. 57, pp. 2175-2186.
Kazanzides, Peter et al., "Force Sensing and Control for a Surgical Robot," Int. Conference on Robotics and Automation, May 1992, Nice, France; pp. 612-617, vol. 1, IEEE.
Kazerooni, H. , "Human Extenders," ASME J. Dynamic Systems, Measurements and Control, 1993, pp. 281-290, vol. 115 No. 2(B).
Koizumi, Naoshi et al., "Development of Three-Dimensional Endoscopic Ultrasound System with Optical Tracking," Medical Image Computing and Computer-Assisted Intervention—MICCAI '02, Tokyo, 2002, pp. 60-65, vol. 2488, Springer-Verlag.
Koizumi, Norihiro et al., "Continuous Path Controller of Slave Manipulator in Remote Ultrasound Diagnostic System," Int. Conference on Robotics and Automation (ICRA 2002), 2002, pp. 3368-3373, vol. 4, IEEE.
Kon, Ryan et al., "An open-source ultrasound calibration toolkit," Medical Imaging Ultrasonic Imaging and Signal Processing, 2005, pp. 516-523, vol. 5750, SPIE.
Korein James U. et al., "A Configurable System for Automation Programming and Control," IEEE Conf. on Robotics and Automation. San Francisco, 1986, pp. 1871-1877, vol. 3, IEEE.
Kragic D. et al., "Human-Machine Collaborative Systems for Microsurgical Applications," International Symposium on Robotics Research, 2005, pp. 731-741, vol. 24—Issue 9, Sage Publications.
Krupa, A. et al., "Automatic 3-D Positioning of Surgical Instruments during Laparoscopic Surgery Using Automatic Visual Feedback," Proceedings of the 5th International Conference on Medical Image Computing and Computer-Assisted Intervention-Part, Lecture Notes In Computer Science, 2002, pp. 9-16, vol. 2488, Springer Verlag.
Kumar R., "An Augmented Steady Hand System for Precise Micromanipulation," PhD thesis in Computer Science, The Johns Hopkins University, Baltimore, Apr. 2001, 118 pages.
Kumar, R., et al., "An Augmentation System for Fine Manipulation," Proceedings of the Third International Conference on Medical Image Computing and Computer-Assisted Intervention, Lecture Notes In Computer Science, 2000, vol. 1935, pp. 957-965.
Kumar, Rajesh et al., "Application of Task-Level Augmentation for Cooperative Fine Manipulation Tasks in Surgery," Proceedings of the 4th International Conference on Medical Image Computing and Computer-Assisted Intervention, Lecture Notes In Computer Science, 2001, pp. 1417-1418, vol. 2208, Springer Verlang.
Kumar, Rajesh et al., "Experiments with a Steady Hand Robot in Constrained Compliant Motion and Path Following", 1999, pp. 92-97, IEEE.
Kumar, Rajesh et al., "Preliminary Experiments in Cooperative Human/Robot Force Control for Robot Assisted Microsurgical Manipulation," Conference on Robotics and Automation, 2000, pp. 610-617, vol. 1, IEEE.
Kumar, Rajesh et al., "Preliminary experiments in robot/human microinjection," IEEE/RSJ International Conference on Intelligent Robots and Systems, 2003, pp. 3186-3191, vol. 3, IEEE.
Lacroute, P., "The VolPack Volume Rendering Library," 1995, information downloaded from https://graphics.stanford.edu/software/volpack/, 4 pages.
Lacroute, Philippe G., "Fast Volume Rendering Using a Shear-Warp Factorization of the Viewing Transformation PhD Thesis," Computer Science, Stanford, California, 1995, 236 Pages.
Lang, Samuel J., Xvision 2—A Framework for Dynamic Vision. Masters Thesis, Computer Science, Johns Hopkins University, Baltimore, 2001, pp. 1-49.
Lange, Thomas et al., Augmenting Intraoperative 3D Ultrasound with Preoperative Models for Navigation in Liver Surgery, Medical Image Computing and Computer-Assisted Interventions, 2004, pp. 534-541, vol. 3217, Springer Verlag.
Lau, William W. et al., "Stereo-Based Endoscopic Tracking of Cardiac Surface Deformation," Proceedings of Seventh International Conference on Medical Image Computing and Computer-Assisted Intervention (MICCAI), Lecture Notes in Computer Science, 2004, pp. 494-501, vol. 2, Springer Verlag.
Lavonius, Maija I. et al., "Staging of Gastric Cancer: A Study with Spiral Computed Tomography,Ultrasonography, Laparoscopy, and Laparoscopic Ultrasonography," Surgical Laparoscopy, Endoscopy & Percutaneous Techniques, 2002, pp. 77-81, vol. 12—No. 2, Lippincott Williams & Wilkins, Inc.

(56) References Cited

OTHER PUBLICATIONS

Lawson, Charles L. et al., "Linear least squares with linear inequality constraints Solving Least Squares Problems," 1974, pp. 158-173, Prentice Hall Inc.
Lee Jr, F.T., et al., "CT-monitored Percutaneous Cryoablation in a Pig Liver Model: Pilot Study," Radiology, 1999, vol. 211 (3), pp. 687-692.
Levoy, Marc, "Display of Surfaces from Volume Data," IEEE Computer Graphics and Applications, 1988, pp. 29-37, vol. 8—Iss. 3, IEEE.
Li, Ming and Russell H. Taylor, "Performance of surgical robots with automatically generated spatial virtual fixtures," IEEE International Conference on Robotics and Automation, Barcelona, Spain, Apr. 2005, pp. 217-222.
Li, Ming and Russell H. Taylor, "Spatial Motion Constraints in Medical Robots Using Virtual Fixtures Generated by Anatomy," IEEE International Conference on Robotics and Automation, New Orleans, Apr. 2004, pp. 1270-1275.
Li, Ming et al., "Optimal Robot Control for 3D Virtual Fixture inConstrained ENT Surgery," Proceedings of the Sixth International Conference on Medical Image Computing and Computer Assisted Intervention—MICCAI, Lecture Notes in Computer Science, 2003, pp. 165-172, vol. I, Springer Verlag.
Li, Ming et al., "Recognition of Operator Motions for Real-Time Assistance using Virtual Fixtures," IEEE, Haptics 2003, 11th Symposium on Haptic Interfaces for Virtual Environment and Teleoperator Systems, Mar. 22-23, 2003, pp. 125-131, IEEE.
Loser, Michael H. et al., "A New Robotic System for Visually Controlled Percutaneous Interventions under CT Fluoroscopy," Medical Image Computing and Computer-Assisted Interventions,Lecture Notes in Computer Science, 2000, pp. 887-896, vol. 1935, Springer Verlag.
Loser, Michael H. et al., "Visual servoing for automatic and uncalibrated percutaneous procedures," SPIE Medical Imaging, 2000, pp. 270-281, vol. 3976, SPIE.
Maehara, S. et al., "Laparoscopy-Assisted Hepatectomy Using the Endoclose," Surgical Endoscopy, 2002, vol. 16 (9), pp. 1363-1364.
Maier, Georg, E. et al., "A Dynamically Configurable General Purpose Automation Controller," Proceedings of IFAC/IFIP Symp. on Software for Computer Control, 1986, pp. 47-52, Pergamon Press.
Mala, T. et al., "A Comparative Study of the Short-Term Outcome Following Open and Laparoscopic Liver Resection of Colorectal Metastases," Surg Endosc, 2002, pp. 1059-1063, vol. 16(7), Springer Verlag.
Marayong, Panadda et al., "Spatial Motion Constraints: Theory and Demonstrations for Robot Guidance Using Virtual Fixtures," IEEE International Conference on Robotics and Automation Robotics and Automation, 2003, pp. 1954-1959, vol. 2, No. 14-19, IEEE.
Masamune K., et al., "Development of a MRI Compatible Needle Insertion Manipulator for Stereotactic Neurosurgery," Journal of Image Guided Surgery, 1995, vol. 1, pp. 242-248.
Masamune K., et al., "System for Robotically Assisted Percutaneous Procedures With Computed Tomography Guidance," Journal of Computer-Assisted Surgery, 2001, vol. 6 (6), pp. 370-383.
Masamune Ken et al., "Development of CT-PAKY frame system—CT image guided needle puncturing manipulator and a single slice registration for urological surgery," Proc. 8th annual meeting of Japanese Society for Computer Aided Surgery (JSCAS), 1999, pp. 89-90.
Masamune, Ken et al., "Development of a MRI Compatible Needle Insertion Manipulator for Stereotactic Neurosurgery," Image Guid Surg, 1995, pp. 165-172.
Masamune, Ken H. et al., "A Newly Developed Stereotactic Robot with Detachable Drive for Neurosurgery," 1st International Conference on Medical Image Computing and Computer-Assisted Intervention—MICCAI,Cambridge, Massachusetts; Springer, Oct. 11-13, 1998, pp. 215-222, vol. 1496.
Mayer, Hermann et al., "Skill Transfer and Learning by Demonstration in a Realistic Scenario of Laparoscopic Surgery," International Conference on Humanoids, 2003, 17 pages, IEEE.
Mayer, Hermann et al., "The Endo [PA]R System for Minimally Invasive Robotic Surgery," IEEE/RSJ International Conference on Intelligent Robots and Systems (IROS), 2004, pp. 3637-3642, vol. 4, IEEE.
Megali, Giusepp et al., "A Computer-Assisted Robotic Ultrasound-Guided Biopsy System for Video-Assisted Surgery," Proceedings of the 4th International Conference on Medical Image Computing and Computer-Assisted Intervention, Lecture Notes In Computer Science, 2001, pp. 343-350, vol. 2208, Springer-Verlag.
Menack, M. et al., "Staging of pancreatic and ampullary cancers for resectability using laparoscopy with laparoscopic ultrasound," Surg Endosc, 2001, pp. 1129-1134, vol. 15—No. 10, Springer-Verlag.
Menon, Mani, "Vattikuti Institute prostatectomy, a technique of robotic radical prostatectomy for management of localized carcinoma of the prostate: experience of over 1100 cases," Urol Clin N Am, 2004, pp. 701-717, vol. 31.
Merola, Stephen et al., "Comparison of Laparoscopic Colectomy With and Without the Aid of a Robotic Camera Holder," Surg Laparosc Endosc Percutan Tech, 2002, pp. 45-61, vol. 12—No. 1, Lippincott Williams & Wilkins, Inc.
Migga, Michael I. et al., "intraoperative Registration of the Liver for Image-Guided Surgery System," The International Society for Optical Engineering (SPIE), Medical Imaging 2003: Visualization, Image-Guided Procedures, and Display; San Diego, CA, Ed. Robert L. Galloway, 2003, pp. 350-359, vol. 5029.
Mitsuishi M., et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Mitsuishi, Mamoru et al., "Remote Ultrasound Diagnostic System," Conf. on Robotics and Automation, 2001, pp. 1567-1574, vol. 2, IEEE.
Mourgues, Fabienet al., "Flexible Calibrations of Actuated Stereoscopic Endoscope for Overlay in Robot Assisted Surgery," Proceedings of the 5th International Conference on Medical Image Computing and Computer-Assisted Intervention—Part I, Lecture Notes In Computer Science, 2002, pp. 25-34, vol. 2488, Springer-Verlag.
Muratore, Diane M. et al., "Beam Calibration Without a Phantom for Creating a 3D Freehand Ultrasound System," Ultrasound in Medicine and Biology, 2001, pp. 1557-1566, vol. 27—No. 11, Elsevier.
Nakakura, Eric K et al., "Hepatocellular Carcinoma: Current Management Recommendations," Advances on Oncology, 2000, pp. 12-18, vol. 16—No. 2.
Nelson, Thomas R. et al., "Interactive Acquisition, Analysis, and Visualization of Sonographic Volume Data," International Journal of Imaging Systems and Technology, 1997, pp. 26-37, vol. 8, John Wiley & Sons, Inc.
Nelson, Thomas, R. et al., "Three-dimensional ultrasound imaging," Ultrasound in Medicine & Biology, 1998, pp. 1243-1270, vol. 24—No. 9, Elsevier.
Novotny Paul M. et al., "Tool Localization in 3D Ultrasound Images," Medical Image Computing and Computer-Assisted Intervention, 2003, pp. 969-970, vol. 2879, Springer.
Ohbuchi R., et al., "Incremental Volume Reconstruction and Rendering for 3D Ultrasound Imaging," The International Society of Optical Engineering, 1992, vol. 1808, pp. 312-323.
Park, Shinsuk et al., "Virtual Fixtures for Robotic Cardiac Surgery," Proceedings of the 4th International Conference on Medical Image Computing and Computer-Assisted Intervention, 2001, pp. 1419-1420, vol. 2208, Springer-Verlag.
Patriciu A., et al., "Motion-based Robotic Instrument Targeting under C-Arm Fluoroscopy," Medical Image Computing and Computer-Assisted Interventions, 2000, vol. 1935, pp. 988-998.
Payandeh S., et al., "On Application of Virtual Fixtures as an Aid for Telemanipulation and Training," Proceedings 10th Symposium on Haptic Interfaces for Virtual Environment and Teleoperator Systems (HAPTICS),Mar. 2002, pp. 18-23.

(56) References Cited

OTHER PUBLICATIONS

PCT/US06/21852 International Search Report dated Nov. 2, 2006, 3 pages.
PCT/US06/21852 Written Opinion of the International Search Authority dated Nov. 2, 2006, 6 pages.
PCT/US06/40754 International Search Report dated Jul. 11, 2007, 4 pages.
PCT/US06/40754 Written Opinion of the International Search Authority dated Apr. 23, 2008, 8 pages.
Podnos Y.D., et al., "Laparoscopic Ultrasound with Radiofrequency Ablation in Cirrhotic Patients with Hepatocellular Carcinoma: Technique and Technical Considerations," American Surgeon, Dec. 2001, vol. 67 (12), pp. 1181-1184.
Poulose B.K., et al., "Human vs Robotic Organ Retraction During Laparoscopic Nissen Fundoplication," Surgical Endoscopy, 1999, vol. 13, pp. 461-465.
Prager Richard et al., "Practical segmentation of 3D ultrasound," In Proceedings of Medical Image Understanding and Analysis, 1999, pp. 161-164.
Prager Richard et al., "Rapid Calibration for 3D Freehand Ultrasound," Ultrasound in Medicine and Biology, 1998, pp. 855-869, vol. 24—No. 6, Elsevier.
Prasad Srinivas K. et al., "A Modular 2-DOF Force-Sensing Instrument for Laparoscopic Surgery," Proceedings of the Sixth International Conference on Medical Image Computing and Computer Assisted Intervention—MICCAI,Lecture Notes in Computer Science, 2003, pp. 279-286, vol. I, Springer.
Prasad, Srinivas K. et al., "A minimally invasive approach to pelvic osteolysis," 2002, in Proc. Computer-Assisted Orthopaedic Surgery (CAOS), pp. 349-350.
Ramey, N. A., "Stereo-Based Direct Surface Tracking with Deformable Parametric Models," Thesis submitted to The Johns Hopkins University, Maryland, Apr. 2003, 104 pages.
Ramey, Nicholas A. et al., "Evaluation of Registration Techniques in a robotic approach to pelvic osteolysis," International Proceedings of Computer Assisted Orthopaedic Surgery (CAOS), 2004, pp. 26-27.
Ratner, Lloyd E. et al, "Laparoscopic live donor nephrectomy removes disincentives to live donation," Transplantation, 1997, pp. 3402-3403, vol. 29—Issue 8, Elsevier.
Ratner, Lloyd E. et al., "Laparoscopic live donor nephrectomy," Transplantation, 1995, pp. 1047-1049.
Rau, Beate, M. eta al., "Is There Additional Information From Laparoscopic Ultrasound in Tumor Staging", Digestive Surgery, 2002, pp. 479-483, vol. 19—No. 6.
Rohling, Robert et al., "Three-dimensional spatial compounding of ultrasound images," Medical Image Analysis, 1996, pp. 177-193, vol. 1—No. 3, Oxford University Press.
Rohling, Robert N. et al., "Radial basis function interpolation for 3-d ultrasound," CUED/F-INFENG/TR 327, Cambridge University, Jul. 1998, 28 Pages.
Rosen J., et al., "The BlueDRAGON—A System for Measuring the Kinematics and the Dynamics of Minimally Invasive Surgical Tools In-Vivo," Proceedings of the 2002 IEEE International Conference on Robotics & Automation, 2002, pp. 1876-1881.
Rosenberg, Louis B., "Virtual Fixtures: Perceptual Tools for Telerobotic Manipulation," IEEE Virtual Reality International Symposium, 1993, pp. 76-82, IEEE.
Rothbaum Daniel L. et al., "Robot-assisted stapedotomy: micropick fenestration of the stapes footplate," Otolaryngology—Head and NeckSurgery, 2002, pp. 417-426, vol. 127.
Rothbaum Daniel L. et al., "Task Performance in stapedotomy: Comparison between surgeons of different experience levels," Otolaryngology—Head and Neck Surgery, 2003, pp. 71-77, vol. 128—No. 1.
Roy, Jaydeep, "Advances in the design, analysis and control of force controlled robots," Master's Thesis, Mechanical Engineering, Johns Hopkins University, Baltimore, 2001, 210 Pages.
Sakas, Georgios et al., "Extracting surfaces from fuzzy 3D-Ultrasound data," Proceedings of the 22nd annual conference on Computer graphics and interactive techniques, 1995, pp. 465-474.
Salcudean, Septimiu E. et al., "A Robot System for Medical Ultrasound," 9th International Symposium of Robotics Research (ISRR'99), 1999, pp. 195-202.
Santambrogio, R. et al., "Ultrasound-Guided Interventional Procedures of the Liver During Laparoscopy: Technical Considerations," Surg Endosc, 2002, pp. 349-354, Springer-Verlag.
Schorr, O., et al., "Distributed Modular Computer-Integrated Surgical Robotic Systems: Architecture for Intelligent Object Distribution," Proceedings of the Third International Conference on Medical Image Computing and Computer-Assisted Intervention, Lecture Notes In Computer Science, 2000, vol. 1935, pp. 979-987.
Schreiner, Steve et al., "A system for percutaneous delivery of treatment with a fluoroscopically-guided robot," Proceedings of the First Joint Conference on Computer Vision, Virtual Reality and Robotics in Medicine and Medial Robotics and Computer-Assisted Surgery,Lecture Notes in Computer Science, 1997, pp. 747-756, Springer-Verlag.
Schweikard, Achim et al., "Motion Planning in Stereotaxic Radiosurgery," IEEE Transactions on Robotics and Automation, 1993, pp. 909-916, vol. 1, IEEE.
Scott D.J., et al., "Accuracy and Effectiveness of Laparoscopic vs Open Hepatic Radiofrequency Ablation," Surgical Endoscopy, Feb. 2001, vol. 15 (2),pp. 135-140.
Simaan, Nabil et al., "A Dexterous System for Laryngeal Surgery: Multi-Backbone Bending Snake-like Slaves for Teleoperated Dextrous Surgical Tool Manipulation," IEEE International Conference on Robotics and Automation, 2004, pp. 351-357, IEEE.
Simaan, Nabil et al., "High Dexterity Snake-Like Robotic Slaves for Minimally Invasive Telesurgery of the Upper Airway," MICCAI 2004—the 7th International Conference on Medical Image Computing and Computer-Assisted Intervention, 2004, pp. 17-24.
Solomon S.B., et al., "Robotically Driven Interventions: A Method of Using CT Fluoroscopy without Radiation Exposure to the Physician," Radiology, 2002, vol. 225, pp. 277-282.
Solus-3D Ultrasound Project in Obstetrics and Gynaecology, University of Cambridge, http://mi.eng.cam.ac.uk/research/projects/Solus/, downloaded Jul. 5, 2007, 4 pages.
Sommer, Graham et al., "Liver tumors: utility of characterization at dual frequency US," Radiology, 1999, pp. 629-636, vol. 211—No. 3.
Steele, Micah R. et al., "Shared control between human and machine: using a haptic steering wheel to aid in land vehicle guidance," Human Factors and Ergonomics Society 45th Annual Meeting , Minneapolis, Minnesota, 2001, pp. 1671-1675.
Steen, Erik et al., "Volume Rendering of 3D Medical Ultrasound Data Using Direct Feature Mapping," IEEE Transactions on Medical Imaging, 1994, pp. 517-525, vol. 13—Iss. 3, IEEE.
Stefansic, James D. et al., "Registration of Physical Space to Laparoscopic Image Space for Use in Minimally Invasive Hepatic Surgery," IEEE Transactions on Medical Imaging, 2000, pp. 1012-1023, vol. 19—No. 10, IEEE.
Stetten, George D et al., "Overlaying Ultrasound Images on Direct Vision," Journal of Ultrasound in Medicine, 2001, pp. 235-240, vol. 20—No. 3.
Stewart, Charles V. et al., "The Dual-Bootstrap Iterative Closest Point Algorithm With Application to Retinal Image Registration," IEEE Transactions on Medical Imaging, Nov. 2003, pp. 1379-1394, vol. 22—No. 11, IEEE.
Stoainovici D., et al., "Robotic Telemanipulation for Percutaneous Renal Access," in 16th World Congress On Endourology, New York City, Sep. 3-6, 1998, Poster Session 17-5, p. S201.
Stoianovici, Dan et al., "Robotic For Precise Percutaneous Needle Insertion," In Thirteenth Annual Meeting of the Society for Urology and Engineering. San Diego, May 1998, pp. 4.
Stoianovici, Dan, "A Modular Surgical Robotic System for Image Guided Percutaneous Procedures," Proceedings of the First International Conference on Medical Image Computing and Computer-Assisted Intervention, pp. 404-410, vol. 1496, Springer-Verlag, 1998.

(56) References Cited

OTHER PUBLICATIONS

Stoll, Jeff, "Ultrasound-based servoing of manipulators for telesurgery," Telemanipulator and Telepresence Technologies VIII Conference, 2001, pp. 78-85, SPIE.
Sublett, John W. et al. "Design and implementation of a digital teleultrasound system for real-time remote diagnosis," 8th IEEE Symposium on Computer-Based Medical Systems, IEEE Computer Society Press, Jun. 9-10, 1995, pp. 292-298.
Suramo, I. et al., "Cranio-caudal movements of the liver, pancreas and kidneys in respiration," Acta Radiologica: Diagnosis, 1984, pp. 129-131, vol. 25, Radiological Societies.
Susil, Robert, C. et al., "A Single Image Registration Method for CT Guided Interventions," 2nd International Symposium on Medical Image Computing and Computer-Assisted Interventions (MICCAI' 99),Lecture Notes in Computer Science, 1999, pp. 798-808, vol. 1679, Springer-Verlag.
Szeliski, Richard, "Motion Estimation with Quadtree Splines," IEEE 5th International Conference on Computer Vision, 1995, pp. 757-763, vol. 18—Issue. 12, IEEE Computer Society Washington, DC, USA.
Taylor R., et al., "A Telerobotic System for Augmentation of Endoscopic Surgery," in IEEE Conference on Engineering in Medicine and Biology, 1992, vol. 14, pp. 1054-1056.
Taylor R.H., et al., "A Computational Architecture for Programmable Automation Research," Intelligent Robots and Computer Vision, 1986, vol. 726, pp. 438-440.
Taylor R.H., et al., Table of Contents, "Computer-Integrated Surgery," Technology and Clinical Applications, The MIT Press, Cambridge, MA, 1996, 8 pages.
Taylor, R.H., "Medical Robotics and Computer-Integrated Surgery," Handbook of Industrial Robotics, Second Edition, 1999, pp. 1213-1227, Chapter 65, John Wiley & Sons.
Taylor, R.H., et al., "A General Purpose Control Architecture for Programmable Automation Research," Proceedings of the Third International Symposium on Robotics, 1986, pp. 165-173, MIT Press.
Taylor, Russell H. "An Image-directed Robotic System for Precise Orthopaedic Surgery," IEEE Transactions on Robotics mid Automation, 1994, pp. 261-275, vol. 10—No. 3, IEEE.
Taylor, Russell H. "Medical Robots," in Computer and Robotic Assisted Knee and Hip Surgery, 2004, pp. 54-59, Oxford Press.
Taylor, Russell H. "The Planning and Execution of Straight Line Manipulator Trajectories," IBM Journal of Research and Development, 1979, pp. 424-436, vol. 23—Issue 4.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Taylor, Russell H. et al., "An Image-directed Robotic System for Hip Replacement Surgery," J. Robotics Society of Japan, 1990, pp. 615-620, vol. 8—issue 5.
Taylor, Russell H. et al., "Computer-Integrated Revision Total Hip Replacement Surgery: Concept and Preliminary Results," 1999, Medical image analysis, pp. 301-319, vol. 3—Issue 3, Oxford University Press.
Taylor, Russell H. et al., "Medical Robotics in Computer-Integrated Surgery," IEEE Transactions on Robotics md Automation, 2003, pp. 765-781, vol. 19—No. 5, IEEE.
Taylor, Russell H., "Robotics in Orthopedic Surgery," In Computer Assisted Orthopaedic Surgery (CAOS), L.P. Nolte and R. Ganz, Editors. 1999, Hogrefe and Huber, 1999, pp. 35-41.
Taylor, Russell H., et al., "Chapter 46: A Telerobotic Assistant for Laparoscopic Surgery," in Computer-Integrated Surgery, R. H. Taylor, et al., Editors, 1996, MIT Press, pp. 581-592.
Taylor, Russell, H et al., "A Steady-Hand Robotic System for Microsurgical Augmentation," International Journal of Robotics Research, 1999, pp. 1201-1210, vol. 18—No. 12, Springer-Verlag.
Taylor, Russell, H et al., "AML A Manufacturing Language," The International Journal of Robotics Research, 1982, pp. 19-41, vol. 1—No. 3, SAGE Publications.
Taylor, Russell, H et al., "The Architecture of an Integrated Robot System," First Int. Conf. on Advanced Robotics (ICAR)., 1983, pp. 389-398.
Taylor, Russell, H. et al., "An Integrated Robot Systems Architecture," Proceedings of the IEEE, 1983, pp. 842-856, vol. 71—Issue 7, IEEE.
Taylor, Russell, H. et al., "Redundant Consistency Checking in a Precise Surgical Robot," in 12'th Annual Conference on Engineering in Medicine and Biology, 1990, pp. 1933-1935, vol. 12—No. 5, IEEE.
Teistler, Michael et al., "Virtual Tomography: A New Approach to Efficient Human-Computer Interaction for Medical Imaging," Proc. of SPIE,, The International Society for Optical Engineering (SPIE), Medical Imaging 2003: Visualization, Image-Guided Procedures, and Display; San Diego, CA, Ed. Robert L. Galloway, 2003, pp. 512-519, vol. 5029.
Tewari, Ashutosh et al., "Technique of da Vinci Robot-Assisted Anatomic Radical Prostatectomy," Urology, 2002, pp. 569-572,vol. 60—No. 4, Elsevier.
Toyama, Kentaro et al., "Incremental Focus of Attention for Robust Vision-based Tracking," International Journal of Computer Vision, 1999, pp. 45-63, vol. 35—No. 1, Kluwer Academic Publishers.
Troccaz, Jocelyne et al., "The use of localizers, robots, and synergistic devices in CAS," Proceedings of the First Joint Conference on Computer Vision, Virtual Reality and Robotics in Medicine and Medial Robotics and Computer-Assisted Surgery,Lecture Notes in Computer Science, 1997, pp. 727-736, vol. 1205, Springer-Verlag.
Uecker, Darrin R. et al., "A Speech-Directed Multi-Modal Man-Machine Interface for Robotically Enhanced Surgery," 1994, pp. 176-183.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Vilchis, Adriana et al., "A New Robot Architecture for Tele-Echography," IEEE Trans. Robotics & Automation, pp. 922-926, 2003, vol. 19—No. 5, IEEE.
Viswanathan, Anand et al., "Immediate Ultrasound Calibration with Three Poses and Minimal Image Processing," MICCAI, 2004, pp. 446-454, vol. 2, Springer-Verlag.
Webster R.J. et al., "Nonholonomic Modeling of Needle Steering," The International Journal of Robotics Research, 2006, vol. 25 (5-6), pp. 509-525.
Webster Robert J. et al., "Design Considerations for Robotic Needle Steering," International Conference on Robotics and Automation, 2005, pp. 3588-3594, IEEE.
Wei, Zhouping et al. "Robot-assisted 3D-TRUS guided prostate brachytherapy: system integration and validation," Medical Physics, 2004, pp. 539-548, vol. 31—No. 3.
Wengert, C., "Camera Calibration Toolbox for Matlab," http://www.vision.caltech.edu/bouguetj/calib_doc/, downloaded Oct. 24, 2006, 9 pages.
Wilhelm, Dirk et al., "Electromagnetically Navigated Laparoscopic Ultrasound," Surg. Technol. Int, 2003, pp. 50-54, vol. 11.
Wood Thomas F. et al., "Radiofrequency ablation of 231 Unresectable hepatic tumors:indications, limitations, and complications," Ann. Surg. Oncol, 2000, pp. 593-600, vol. 7, Lippincott Williams & Wilkins.
Wu, Xiaohui et al., "A Framework for Calibration of Electromagnetic Surgical Navigation Systems," IEEE RSJ International Conference on Intelligent Robot Systems (IROS), 2003, pp. 547-552, vol. 1, IEEE.
Xu, Sheng et al., "3D Motion Tracking of Pulmonary Lesions Using CT Fluoroscopy Images for Robotically Assisted Lung Biopsy," Proc. SPIE. 5367, Medical Imaging 2004: Visualization, Image-Guided Procedures, and Display, 394. (May 5, 2004), pp. 394-402.
Yamagata H., et al., "Development of a New Display Method for Compound 3D Ultrasound Images: Fusion 3D Images From B-mode and 3D Doppler Images," 1999, vol. 70, pp. 43-46.
Yao, Jianhua et al., "A C-arm fluoroscopy-guided progressive cut refinement strategy using a surgical robot," Computer Aided Surgery, 2000, pp. 373-390, vol. 5—No. 6, Wiley-Liss, Inc.

(56) References Cited

OTHER PUBLICATIONS

Yao, Jianhua et al., "Deformable registration between a statistical born density atlas and X-ray images," Second International Conference on Computer Assisted Orthopaedic Surgery, 2002, pp. 168-169.
Yao, Jianhua, et al., "A Progressive Cut Refinement Scheme for Revision Total Hip Replacement Surgery Using C-arm Fluoroscopy," Proceedings of the 2nd International Conference on Medical Image and Computer-Assisted Intervention (MICCAI'99), Springer-Verlag, 1999, pp. 1010-1019, vol. 1679.
Zacherl, Johannes et al., "Current value of intraoperative sonography during surgery for hepatic neoplasms," World J Surg, 2002, pp. 550-554, vol. 26—No. 5.
Zhang, Z., "A Flexible New Technique for Camera Calibration," Technical report MSR-TR-98-71, Microsoft Research, Microsoft Corporation, Redmond, WA, Dec. 1998, pp. 1-21.
Extended European Search Report for Application No. 16195634.7, dated Jul. 11, 2017, 10 pages.
Extended European Search Report for Application No. EP16195633.9, dated Mar. 17, 2017, 7 pages.
Extended European Search Report for Application No. EP19164568.8, dated Jun. 28, 2019, 6 pages.
Office Action dated Jun. 9, 2016 for European Application No. 06817132.1 filed Oct. 19, 2006, 3 pages.
Office Action dated Sep. 28, 2014 for Chinese Application 201310052673.7 filed Oct. 19, 2006, 9 pages.
Partial European Search Report for Application No. EP16195634.7, dated Mar. 15, 2017, 7 pages.
Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

* cited by examiner

AUXILIARY IMAGE DISPLAY AND MANIPULATION ON A COMPUTER DISPLAY IN A MEDICAL ROBOTIC SYSTEM

CROSS REFERENCE TO RELATED APPLICATIONS

This application is a continuation of U.S. application Ser. No. 15/139,682 (filed Apr. 27, 2016), which is a division of U.S. application Ser. No. 11/583,963 (filed Oct. 19, 2006), abandoned, which claims priority to U.S. provisional Application No. 60/728,450 (filed Oct. 20, 2005), each of which is incorporated herein by reference.

FIELD OF THE INVENTION

The present invention generally relates to medical robotic systems and in particular, to the displaying and manipulating of auxiliary images on a computer display in a medical robotic system.

BACKGROUND

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using medical robotic systems is strong and growing.

One example of a medical robotic system is the daVinci® Surgical System from Intuitive Surgical, Inc., of Sunnyvale, Calif. The daVinci® system includes a surgeon's console, a patient-side cart, a high performance 3-D vision system, and Intuitive Surgical's proprietary EndoWrist™ articulating instruments, which are modeled after the human wrist so that when added to the motions of the robotic arm assembly holding the surgical instrument, they allow at least a full six degrees of freedom of motion, which is comparable to the natural motions of open surgery.

The daVinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intra-operative imagery.

In addition to primary imagery being displayed on the display screen, it is also desirable at times to be able to concurrently view auxiliary information to gain better insight or to otherwise assist in the medical procedure being performed. The auxiliary information may be provided in various modes such as text information, bar graphs, two-dimensional picture-in-picture images, and two-dimensional or three-dimensional images that are registered and properly overlaid with respect to their primary image counterparts.

For auxiliary images, the images may be captured pre-operatively or intra-operatively using techniques such as ultrasonography, magnetic resonance imaging, computed axial tomography, and fluoroscopy to provide internal details of an anatomic structure being treated. This information may then be used to supplement external views of the anatomic structure such as captured by a locally placed camera.

Although there are a plethora of auxiliary information sources as well as manners of displaying that information, improvements in the display and manipulation of auxiliary images is still useful to better assist surgeons in performing medical procedures with medical robotic systems.

BRIEF SUMMARY

Accordingly, one object of various aspects of the present invention is a method for displaying auxiliary information including the effect of a therapeutic procedure as an overlay to or otherwise associated with an image of an anatomic structure being treated at the time by the procedure.

Another object of various aspects of the present invention is a method for displaying a user selected portion at a user specified magnification factor of a volume rendering of an auxiliary image of an anatomic structure as a registered overlay to a primary image of the anatomic structure on a computer display screen.

Another object of various aspects of the present invention is a medical robotic system having a master input device that may be used to manually register images in a three-dimensional space of a computer display.

Another object of various aspects of the present invention is a medical robotic system having a master input device that may be used to define cut-planes of a volume rendering of an anatomic structure in a three-dimensional space of a computer display.

Another object of various aspects of the present invention is a medical robotic system having a master input device that may be used to selectively modify portions or details of a volume rendering of an anatomic structure in a three-dimensional space of a computer display.

Another object of various aspects of the present invention is a medical robotic system having a master input device that may be used to vary display parameters for a rendering of an anatomic structure being displayed on a computer display screen.

Still another object of various aspects of the present invention is a medical robotic system having a master input device that may be switched between an image capturing mode wherein the master input device controls movement of an image capturing device, and an image manipulating mode wherein the master input device controls display and manipulation of images captured by the image capturing device on a computer display screen.

These and additional objects are accomplished by the various aspects of the present invention, wherein the embodiments of the invention are summarized by the claims that follow below.

Additional objects, features and advantages of the various aspects of the present invention will become apparent from the following description of its preferred embodiment, which description should be taken in conjunction with the accompanying drawings.

DETAILED DESCRIPTION

Figure 1:
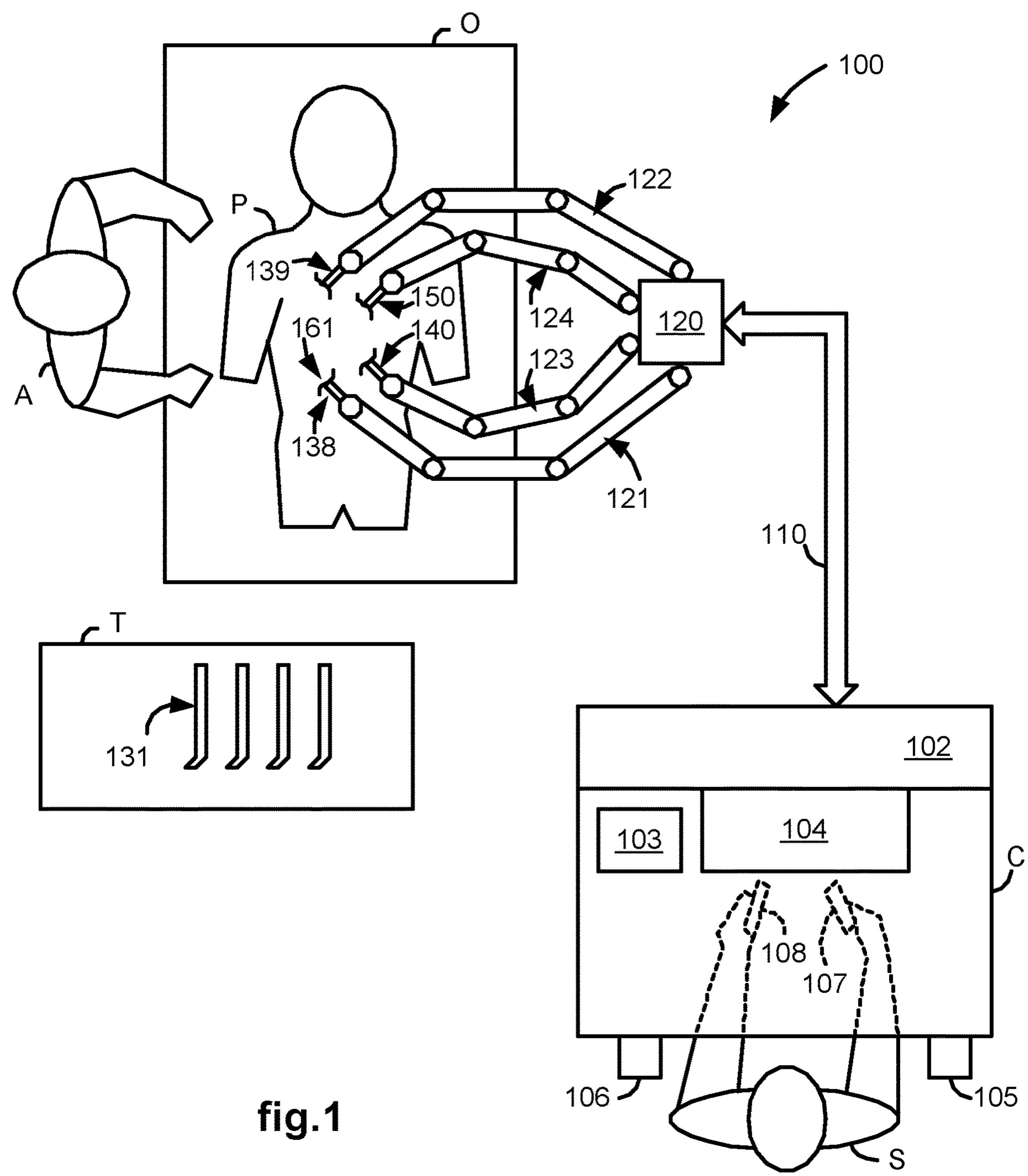
FIG. 1 illustrates a top view of an operating room employing a medical robotic system utilizing aspects of the present invention.

FIG. 1 illustrates, as an example, a top view of an operating room employing a medical robotic system. The medical robotic system in this case is a Minimally Invasive Robotic Surgical ("MIRS") System 100 including a Console ("C") utilized by a Surgeon ("S") while performing a minimally invasive diagnostic or surgical procedure with assistance from one or more Assistants ("A") on a Patient ("P") who is reclining on an Operating table ("O").

The Console includes a Master Display 104 (also referred to herein as a "Display Screen" or "computer display screen") for displaying one or more images of a surgical site within the Patient as well as perhaps other information to the Surgeon. Also included are Master Input Devices 107, 108 (also referred to herein as "Master Manipulators"), one or more Foot Pedals 105, 106, a Microphone 103 for receiving voice commands from the Surgeon, and a Processor 102. The Master Input Devices 107, 108 may include any one or more of a variety of input devices such as joysticks, gloves, trigger-guns, hand-operated controllers, grippers, or the like. The Processor 102 is preferably a personal computer that may be integrated into the Console or otherwise connected to it in a conventional manner.

The Surgeon performs a medical procedure using the MIRS System 100 by manipulating the Master Input Devices 107, 108 so that the Processor 102 causes their respectively associated Slave Arms 121, 122 to manipulate their respective removably coupled and held Surgical Instruments 138, 139 (also referred to herein as "Tools") accordingly, while the Surgeon views three-dimensional ("3D") images of the surgical site on the Master Display 104.

The Tools 138, 139 are preferably Intuitive Surgical's proprietary EndoWrist™ articulating instruments, which are modeled after the human wrist so that when added to the motions of the robot arm holding the tool, they allow at least a full six degrees of freedom of motion, which is comparable to the natural motions of open surgery. Additional details on such tools may be found in commonly owned U.S. Pat. No. 5,797,900 entitled "Wrist Mechanism for Surgical Instrument for Performing Minimally Invasive Surgery with Enhanced Dexterity and Sensitivity," which is incorporated herein by this reference. At the operating end of each of the Tools 138, 139 is a manipulatable end effector such as a clamp, grasper, scissor, stapler, blade, needle, needle holder, or energizable probe.

The Master Display 104 has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The Surgeon sits comfortably and looks into this display throughout surgery, making it an ideal place for the Surgeon to display and manipulate 3-D intra-operative imagery.

A Stereoscopic Endoscope 140 provides right and left camera views to the Processor 102 so that it may process the information according to programmed instructions and cause it to be displayed on the Master Display 104. A Laparoscopic Ultrasound ("LUS") Probe 150 provides two-dimensional ("2D") ultrasound image slices of an anatomic structure to the Processor 102 so that the Processor 102 may generate a 3D ultrasound computer model or volume rendering of the anatomic structure.

Each of the Tools 138, 139, as well as the Endoscope 140 and LUS Probe 150, is preferably inserted through a cannula or trocar (not shown) or other tool guide into the Patient so as to extend down to the surgical site through a corresponding minimally invasive incision such as Incision 161. Each of the Slave Arms 121-124 includes a slave manipulator and setup arms. The slave manipulators are robotically moved using motor controlled joints (also referred to as "active joints") in order to manipulate and/or move their respectively held Tools. The setup arms are manually manipulated by releasing normally braked joints (also referred to as "setup joints") to horizontally and vertically position the Slave Arms 121-124 so that their respective Tools may be inserted into the cannulae.

The number of surgical tools used at one time and consequently, the number of slave arms being used in the System 100 will generally depend on the medical procedure to be performed and the space constraints within the operating room, among other factors. If it is necessary to change one or more of the tools being used during a procedure, the Assistant may remove the tool no longer being used from its slave arm, and replace it with another tool, such as Tool 131, from a Tray ("T") in the Operating Room.

Preferably, the Master Display 104 is positioned near the Surgeon's hands so that it will display a projected image that is oriented so that the Surgeon feels that he or she is actually looking directly down onto the surgical site. To that end, an image of the Tools 138, 139 preferably appear to be located substantially where the Surgeon's hands are located even though the observation points (i.e., that of the Endoscope 140 and LUS Probe 150) may not be from the point of view of the image.

In addition, the real-time image is preferably projected into a perspective image such that the Surgeon can manipulate the end effector of a Tool, 138 or 139, through its associated Master Input Device, 107 or 108, as if viewing the workspace in substantially true presence. By true presence, it is meant that the presentation of an image is a true perspective image simulating the viewpoint of an operator that is physically manipulating the Tools. Thus, the Processor 102 transforms the coordinates of the Tools to a perceived position so that the perspective image is the image that one would see if the Endoscope 140 was looking directly at the Tools from a Surgeon's eye-level during an open cavity procedure.

The Processor 102 performs various functions in the System 100. One important function that it performs is to translate and transfer the mechanical motion of Master Input Devices 107, 108 to their associated Slave Arms 121, 122 through control signals over Bus 110 so that the Surgeon can effectively manipulate their respective Tools 138, 139. Another important function is to implement the various methods described herein in reference to FIGS. 4-12.

Although described as a processor, it is to be appreciated that the Processor 102 may be implemented in practice by any combination of hardware, software and firmware. Also, its functions as described herein may be performed by one unit, or divided up among different components, each of which may be implemented in turn by any combination of hardware, software and firmware. When divided up among different components, the components may be centralized in one location or distributed across the System 100 for distributed processing purposes.

Prior to performing a medical procedure, ultrasound images captured by the LUS Probe 150, right and left 2D camera images captured by the stereoscopic Endoscope 140, and end effector positions and orientations as determined using kinematics of the Slave Arms 121-124 and their sensed joint positions, are calibrated and registered with each other.

Slave Arms 123, 124 may manipulate the Endoscope 140 and LUS Probe 150 in similar manners as Slave Arms 121, 122 manipulate Tools 138, 139. When there are only two master input devices in the system, however, such as Master Input Devices 107, 108 in the System 100, in order for the Surgeon to manually control movement of either the Endoscope 140 or LUS Probe 150, it may be required to temporarily associate one of the Master Input Devices 107, 108 with the Endoscope 140 or the LUS Probe 150 that the Surgeon desires manual control over, while its previously associated Tool and Slave Manipulator are locked in position.

Although not shown in this example, other sources of primary and auxiliary images of anatomic structures may be included in the System 100, such as those commonly used for capturing ultrasound, magnetic resonance, computed axial tomography, and fluoroscopic images. Each of these sources of imagery may be used pre-operatively, and where appropriate and practical, intra-operatively.

Figure 2:
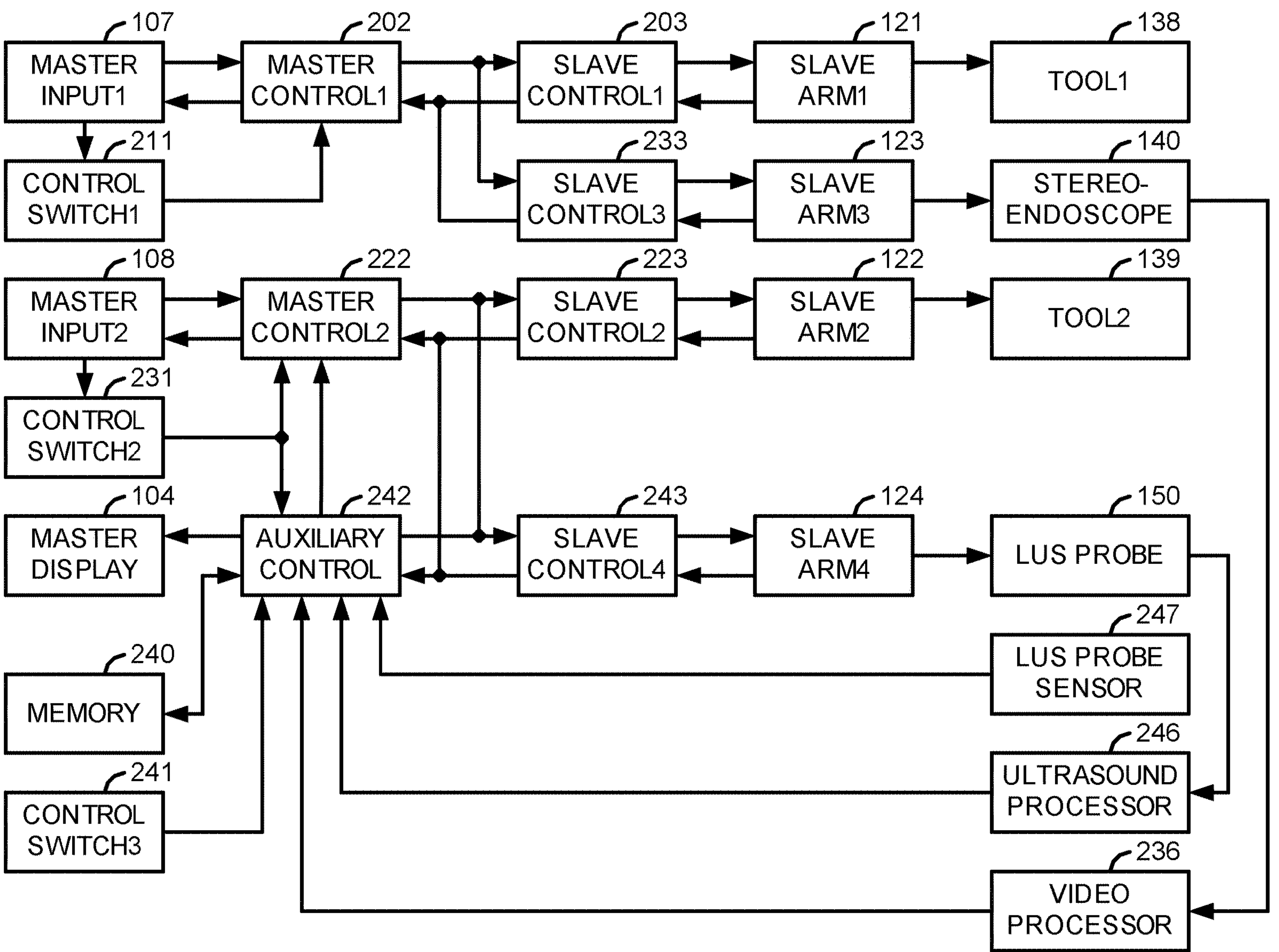
FIG. 2 illustrates a block diagram of a medical robotic system utilizing aspects of the present invention.

FIG. 2 illustrates, as an example, a block diagram of the System 100. In this system, there are two Master Input Devices 107, 108. Master Input Device 107 controls movement of either a Tool 138 or a stereoscopic Endoscope 140, depending upon which mode its Control Switch Mechanism 211 is in, and Master Input Device 108 controls movement of either a Tool 139 or a LUS Probe 150, depending upon which mode its Control Switch Mechanism 231 is in.

The Control Switch Mechanisms 211 and 231 may be placed in either a first or second mode by a Surgeon using voice commands, switches physically placed on or near the Master Input Devices 107, 108, Foot Pedals 105, 106 on the Console, or Surgeon selection of appropriate icons or other graphical user interface selection means displayed on the Master Display 104 or an auxiliary display (not shown).

When Control Switch Mechanism 211 is placed in the first mode, it causes Master Controller 202 to communicate with Slave Controller 203 so that manipulation of the Master Input 107 by the Surgeon results in corresponding movement of Tool 138 by Slave Arm 121, while the Endoscope 140 is locked in position. On the other hand, when Control Switch Mechanism 211 is placed in the second mode, it causes Master Controller 202 to communicate with Slave Controller 233 so that manipulation of the Master Input 107 by the Surgeon results in corresponding movement of Endoscope 140 by Slave Arm 123, while the Tool 138 is locked in position.

Similarly, when Control Switch Mechanism 231 is placed in the first mode, it causes Master Controller 108 to communicate with Slave Controller 223 so that manipulation of the Master Input 108 by the Surgeon results in corresponding movement of Tool 139 by Slave Arm 122. In this case, however, the LUS Probe 150 is not necessarily locked in position. Its movement may be guided by an Auxiliary Controller 242 according to stored instructions in Memory 240. The Auxiliary Controller 242 also provides haptic feedback to the Surgeon through Master Input 108 that reflects readings of a LUS Probe Force Sensor 247. On the other hand, when Control Switch Mechanism 231 is placed in the second mode, it causes Master Controller 108 to communicate with Slave Controller 243 so that manipulation of the Master Input 108 by the Surgeon results in corresponding movement of LUS Probe 150 by Slave Arm 124, while the Tool 139 is locked in position.

Before a Control Switch Mechanism effects a switch back to its first or normal mode, its associated Master Input Device is preferably repositioned to where it was before the switch. Alternatively, the Master Input Device may remain in its current position and kinematic relationships between the Master Input Device and its associated Tool Slave Arm readjusted so that upon the Control Switch Mechanism switching back to its first or normal mode, abrupt movement of the Tool does not occur. For additional details on control switching, see, e.g., commonly owned U.S. Pat. No. 6,659,939 entitled "Cooperative Minimally Invasive Telesurgical System," which is incorporated herein by this reference.

A third Control Switch Mechanism 241 is provided to allow the user to switch between an image capturing mode and an image manipulating mode while the Control Switch Mechanism 231 is in its second mode (i.e., associating the Master Input Device 108 with the LUS Probe 150). In its first or normal mode (i.e., image capturing mode), the LUS Probe 150 is normally controlled by the Master Input Device 108 as described above. In its second mode (i.e., image manipulating mode), the LUS Probe 150 is not controlled by the Master Input Device 108, leaving the Master Input Device 108 free to perform other tasks such as the displaying and manipulating of auxiliary images on the Display Screen 104 and in particular, for performing certain user specified functions as described herein. Note however that although the LUS Probe 150 may not be controlled by the Master Input Device 108 in this second mode of the Control Switch Mechanism 241, it may still be automatically rocked or otherwise moved under the control of the Auxiliary Controller 242 according to stored instructions in Memory 240 so that a 3D volume rendering of a proximate anatomic structure may be generated from a series of 2D ultrasound image slices captured by the LUS Probe 150. For additional details on such and other programmed movement of the LUS Probe 150, see commonly owned U.S. patent application Ser. No. 11/447,668 entitled "Laparoscopic Ultrasound Robotic Surgical System," filed Jun. 6, 2006, which is incorporated herein by this reference.

The Auxiliary Controller 242 also performs other functions related to the LUS Probe 150 and the Endoscope 140. It receives output from a LUS Probe Force Sensor 247, which senses forces being exerted against the LUS Probe 150, and feeds the force information back to the Master Input Device 108 through the Master Controller 222 so that the Surgeon may feel those forces even if he or she is not directly controlling movement of the LUS Probe 150 at the time. Thus, potential injury to the Patient is minimized since the Surgeon has the capability to immediately stop any movement of the LUS Probe 150 as well as the capability to take over manual control of its movement.

Another key function of the Auxiliary Control 242 is to cause processed information from the Endoscope 140 and the LUS Probe 150 to be displayed on the Master Display 104 according to user selected display options. Examples of such processing include generating a 3D ultrasound image from 2D ultrasound image slices received from the LUS Probe 150 through an Ultrasound Processor 246, causing either 3D or 2D ultrasound images corresponding to a selected position and orientation to be displayed in a picture-in-picture window of the Master Display 104, causing either 3D or 2D ultrasound images of an anatomic structure to overlay a camera captured image of the anatomic structure being displayed on the Master Display 104, and performing the methods described below in reference to FIGS. 4-12.

Although shown as separate entities, the Master Controllers 202, 222, Slave Controllers 203, 233, 223, 243, and Auxiliary Controller 242 are preferably implemented as software modules executed by the Processor 102, as well as certain mode switching aspects of the Control Switch Mechanisms 211, 231, 241. The Ultrasound Processor 246 and Video Processor 236, on the other hand, may be software modules or separate boards or cards that are inserted into appropriate slots coupled to or otherwise integrated with the Processor 102 to convert signals received from these image capturing devices into signals suitable for display on the Master Display 104 and/or for additional processing by the Auxiliary Controller 242 before being displayed on the Master Display 104.

Although the present example assumes that each Master Input Device is being shared by only one pre-assigned Tool Slave Robotic Arm and one pre-assigned Image Capturing Device Robotic Arm, alternative arrangements are also feasible and envisioned to be within the full scope of the present invention. For example, a different arrangement wherein each of the Master Input Devices may be selectively associated with any one of the Tool and Image Capturing Device Robotic Arms is also possible and even preferably for maximum flexibility. Also, although the Endoscope Robotic Arm is shown in this example as being controlled by a single Master Input Device, it may also be controlled using both Master Input Devices to give the sensation of being able to "grab the image" and move it to a different location or view. Still further, although only an Endoscope and LUS Probe are show in this example, other Image Capturing Devices such as those used for capturing camera, ultrasound, magnetic resonance, computed axial tomography, and fluoroscopic images are also fully contemplated within the System 100, although each of these Image Capturing Devices may not necessarily be manipulated by one of the Master Input Devices.

Figure 3:
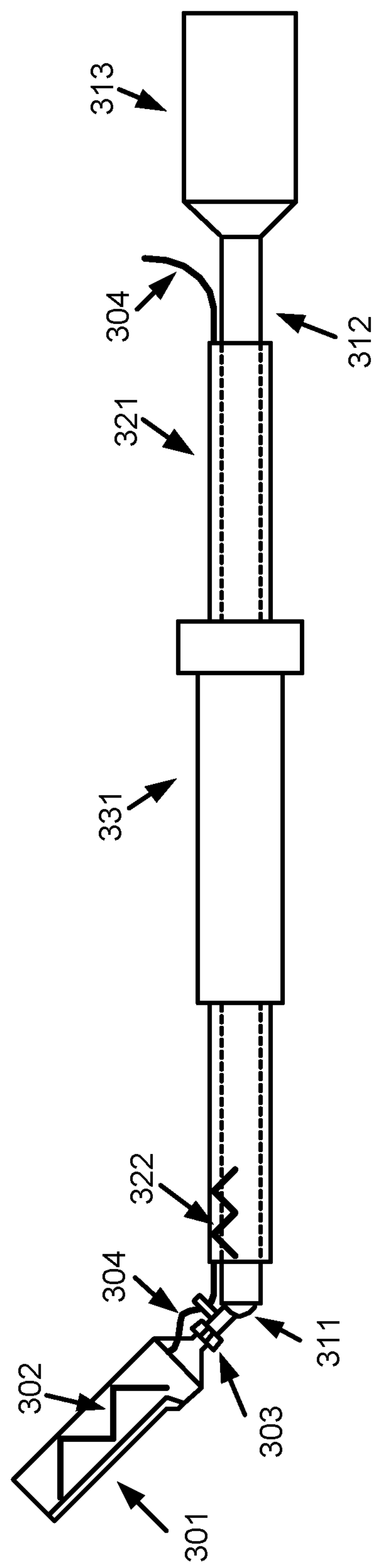
FIG. 3 illustrates a laparoscopic ultrasound probe useful for a medical robotic system utilizing aspects of the present invention.

FIG. 3 illustrates a side view of one embodiment of the LUS Probe 150. The LUS Probe 150 is a dexterous tool with preferably two distal degrees of freedom. Opposing pairs of Drive Rods or Cables (not shown) physically connected to a proximal end of the LUS Sensor 301 and extending through an internal passage of Elongated Shaft 312 mechanically control pitch and yaw movement of the LUS Sensor 301 using conventional push-pull type action.

The LUS Sensor 301 captures 2D ultrasound slices of a proximate anatomic structure, and transmits the information back to the Processor 102 through LUS Cable 304. Although shown as running outside of the Elongated Shaft 312, the LUS Cable 304 may also extend within it. A Clamshell Sheath 321 encloses the Elongate Shaft 312 and LUS Cable 304 to provide a good seal passing through a Cannula 331 (or trocar). Fiducial Marks 302 and 322 are placed on the LUS Sensor 301 and the Sheath 321 for video tracking purposes.

Figure 4:
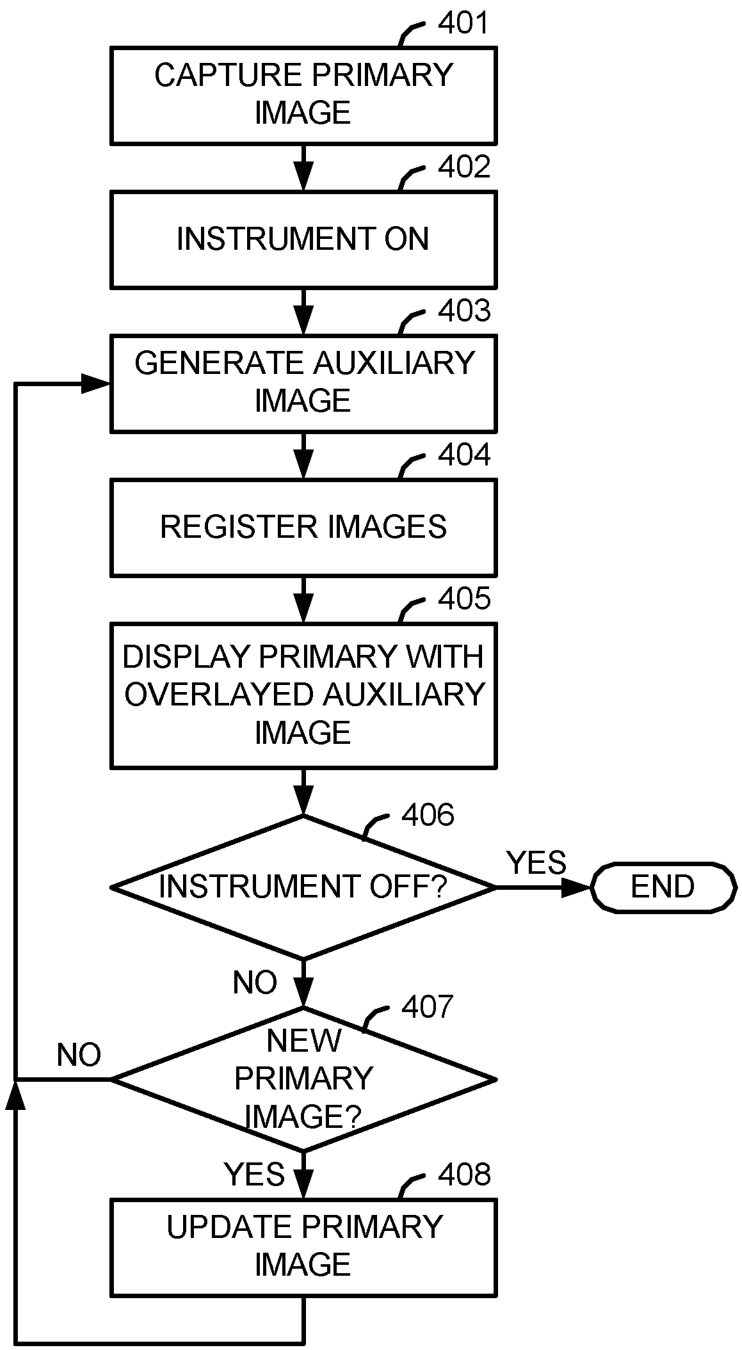
FIG. 4 illustrates a flow diagram of a method for displaying on a computer display screen an effect of a therapeutic procedure being applied by a therapeutic instrument to an anatomic structure, utilizing aspects of the present invention.
Figure 5:
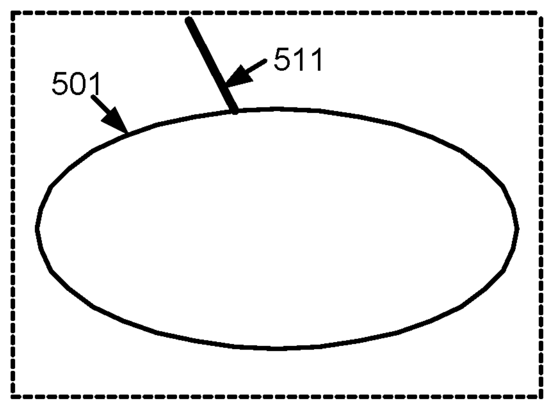
FIG. 5 illustrates an external view of an anatomic structure with a therapeutic instrument inserted in the anatomic structure for performing a therapeutic procedure.

FIG. 4 illustrates, as an example, a flow diagram of a method for displaying the effect of a therapeutic procedure or treatment on the Display Screen 104. In 401, a primary image of an anatomic structure is captured by an image capturing device. As an example, FIG. 5 illustrates a primary image which has been captured by the Endoscope 140 and includes an anatomic structure 501 and therapeutic instrument 511 that has been partially inserted into the anatomic structure 501 in order to perform a therapeutic procedure at a therapy site within the anatomic structure 501. In another application, the therapeutic instrument 511 may only need to touch or come close to the anatomic structure 501 in order to perform a therapeutic procedure.

The primary image may be captured before or during the therapeutic procedure. A primary image captured before the procedure is referred to as being a "pre-operative" image, and a primary image captured during the procedure is referred to as being an "intra-operative" image. When the primary image is a pre-operative image, the image is generally not updated during the procedure, so that the method generally only employs one primary image. On the other hand, when the primary image is an intra-operative image, the image is preferably updated periodically during the procedure, so that the method employs multiple primary images in that case.

Pre-operative images are typically captured using techniques such as Ultrasonography, Magnetic Resonance Imaging (MM), or Computed Axial Tomography (CAT). Intra-operative images may be captured at the surgical or therapeutic site by image capturing devices such as the stereoscopic Endoscope 140 or LUS Probe 150, or they may be captured externally by techniques such as those used to capture the pre-operative images.

In 402 of FIG. 4, the therapeutic instrument is turned on, or otherwise activated or energized, so as to be capable of applying therapy to the anatomic structure within the patient. The instrument generally has a tip for applying the therapeutic energy to abnormal tissue such as diseased or damaged tissue. As one example of such a therapeutic procedure, Radio Frequency Ablation (RFA) may be used to destroy diseased tissue such as a tumor located in an anatomic structure such as the liver by applying heat to the diseased tissue site using an RFA probe. Examples of other procedures include High Intensity Focused Ultrasound (HIFU) and Cauterization. The therapeutic instrument may be one of the Tools 138, 139 attached to Slave Arms 121, 122 so that it may be moved to and manipulated at the therapy site through the master/slave control system by the Surgeon.

In 403, an auxiliary image is generated, wherein the auxiliary image indicates the effect of the therapeutic procedure on the anatomic structure. The auxiliary image may be an actual image of the anatomic structure that has been provided by or generated from information captured by a sensing device which is capable of sensing the effect of the therapeutic procedure. Alternatively, the auxiliary image may be a computer model indicating the effect of the therapy, which may be generated using an empirically derived or otherwise conventionally determined formula of such effect. In this latter case, the computer model is generally a volumetric shape determined by such factors as the geometry of the tip of the therapeutic instrument, the heat or energy level being applied to the anatomic structure by the tip of the therapeutic instrument, and the features of the surrounding tissue of a therapy site being subjected to the therapeutic procedure in the anatomic structure.

Figure 6:
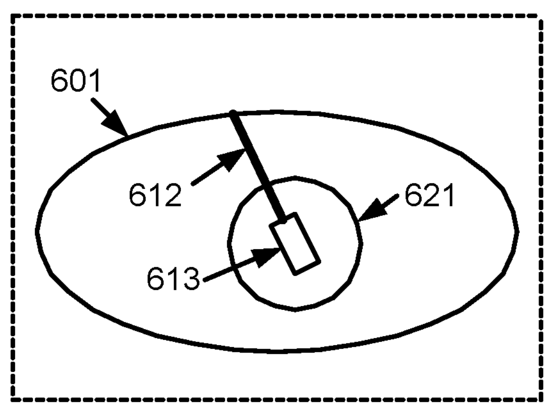
FIG. 6 illustrates an internal view of an anatomic structure with a discernable therapeutic effect shown as captured by a therapy sensing device.

As an example of an auxiliary image provided or otherwise derived from information captured by a sensing device, FIG. 6 illustrates a three-dimensional ultrasound image of an anatomic structure 601 which has been conventionally derived from two-dimensional ultrasound slices captured by the LUS probe 150. In this example, an ablation volume 621 is shown which represents the effect of a therapeutic procedure in which a tip 613 of an RFA probe 612 is being applied to a tumor site of the anatomic structure 601. The growth of the ablation volume in this case is viewable due to changes in tissue properties from the heating and necrosis of the surrounding tissue at the tumor site.

In 404, the primary and auxiliary images are registered so as to be of the same scale and refer to a same position and orientation in a common reference frame. Registration of this sort is well known. As an example, see commonly owned U.S. Pat. No. 6,522,906 entitled "Devices and Methods for Presenting and Regulating Auxiliary Information on an Image Display of a Telesurgical System to Assist an Operator in Performing a Surgical Procedure," which is incorporated herein by this reference.

In 405, the primary image is displayed on the Display Screen 104 while the therapeutic procedure is being performed, with the registered auxiliary image preferably overlaid upon the primary image so that corresponding structures or objects in each of the images appear as the same size and at the same location and orientation on the Display Screen 104. In this way, the effect of the therapeutic procedure is shown as an overlay over the anatomic structure that is being subjected to the procedure.

Figure 7:
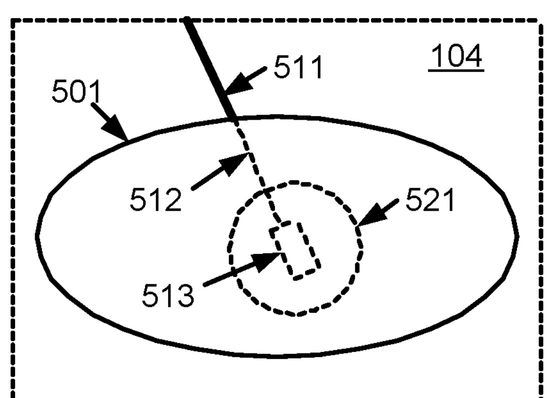
FIG. 7 illustrates a computer display screen displaying an effect of a therapeutic procedure registered to an anatomic structure being treated by the procedure, as generated by a method utilizing aspects of the present invention.

As an example, FIG. 7 shows an exemplary Display Screen 104 in which an auxiliary image, distinguished as a dotted line for illustrative purposes, is overlaid over the primary image of FIG. 5. When the auxiliary image is provided by or derives from information captured by a sensing device, the therapy effect 521, therapeutic instrument 512, and instrument tip 513 is provided by or derived from the captured information. On the other hand, when the therapy effect 521 is generated as a volumetric shaped computer model using an empirically determined formula, the therapeutic instrument 512 and instrument tip 513 may be determined using conventional tool tracking computations based at least in part upon joint positions of its manipulating slave arm.

In 406 of FIG. 4, the method then checks whether the therapeutic instrument has been turned off. If it has, then this means that the therapeutic procedure is over, and the method ends. On the other hand, if the therapeutic instrument is still on, then the method assumes that the therapeutic procedure is still being performed, and proceeds in 407 to determine whether a new primary image has been captured. If no new primary image has been captured, for example, because the primary image is a pre-operative image, then the method jumps back to 403 to update the auxiliary image and continue to loop through 403-407 until the therapeutic procedure is determined to be completed by detecting that the therapeutic instrument has been turned off. On the other hand, if a new primary image has been captured, for example, because the primary image is an intra-operative image, then the method updates the primary image in 408 before jumping back to 403 to update the auxiliary image and continue to loop through 403-408 until the therapeutic procedure is determined to be completed by detecting that the therapeutic instrument has been turned off.

Figures 8, 9:
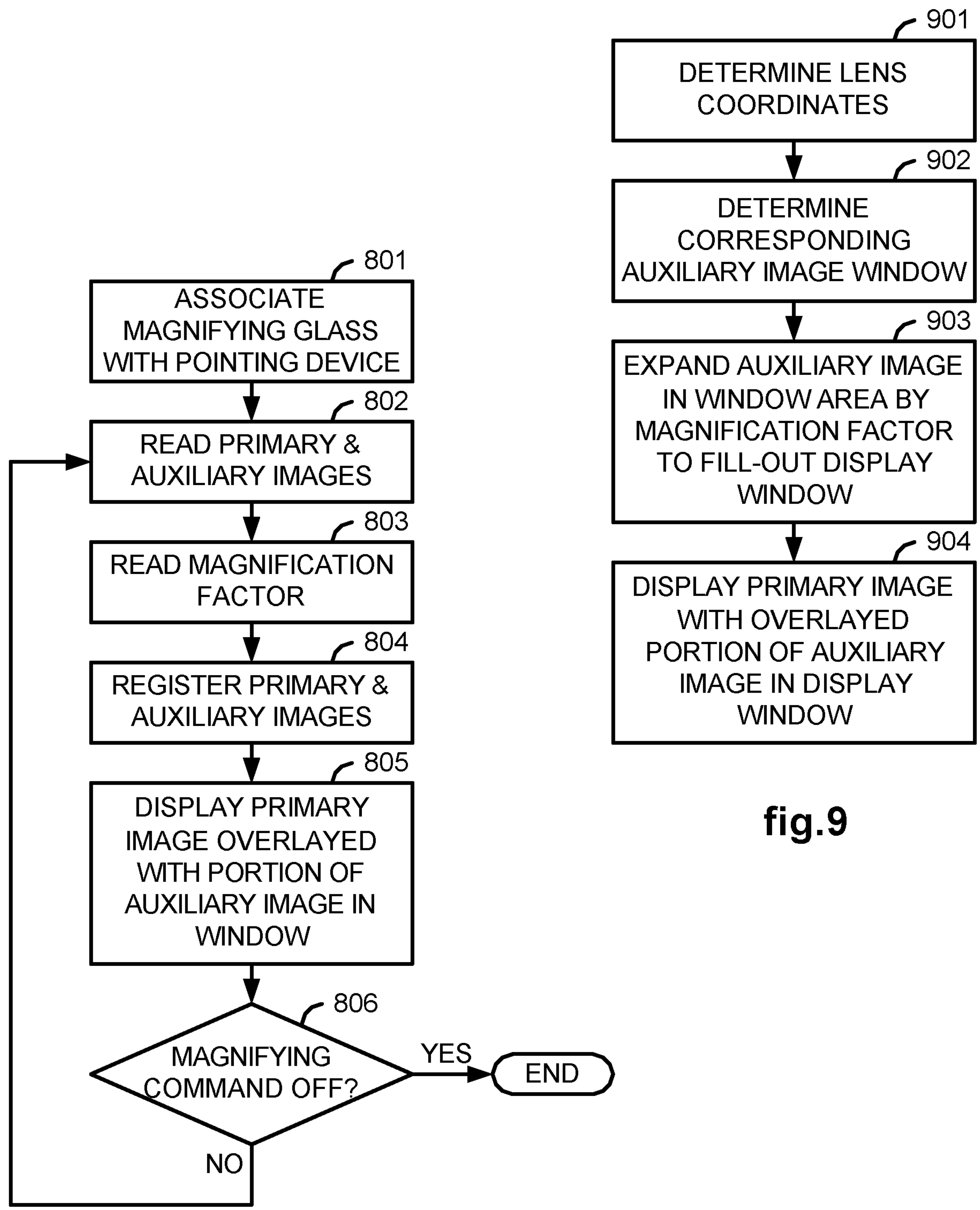
FIG. 8 illustrates a flow diagram of a method for displaying a selected portion of an auxiliary image of an anatomic structure in a user movable magnifying glass on a computer display screen, utilizing aspects of the present invention.
FIG. 9 illustrates a flow diagram of a method for displaying a manipulatable window of an internal view of an anatomic structure at a specified magnification factor, utilizing aspects of the present invention.

FIG. 8 illustrates, as an example, a flow diagram of a method for displaying an auxiliary image of an anatomic structure as a registered overlay to a primary image of the anatomic structure at a user specified magnification in a window defined as the lens area of a magnifying glass whose position and orientation as displayed on the Display Screen 104 is manipulatable by the user using an associated pointing device.

In 801, the method starts out by associating the magnifying glass with the pointing device so that as the pointing device moves, the magnifying glass being displayed on the Display Screen 104 (and in particular, its lens which may be thought of as a window) moves in a corresponding fashion. The association in this case may be performed by "grabbing" the magnifying glass in a conventional manner using the pointing device, or by making the magnifying glass effectively the cursor for the pointing device. Since the Display Screen 104 is preferably a three-dimensional display, the pointing device is correspondingly preferably a three-dimensional pointing device with orientation indicating capability.

In 802, current primary and auxiliary images are made available for processing. The primary image in this example is captured by the Endoscope 140 and the auxiliary captured by the LUS Probe 150. However, other sources for the primary and auxiliary images are also usable and contemplated in practicing the invention, including primary and auxiliary images captured from the same source. As an example of this last case, a high resolution camera may capture images at a resolution greater than that being used to display images on a display screen. In this case, the high resolution image captured by the camera may be treated as the auxiliary image, and the downsized image to be displayed on the display screen may be treated as the primary image.

In 803, a user selectable magnification factor is read. The magnification factor is user selectable by, for example, a dial or wheel type control on the pointing device. Alternatively, it may be user selectable by user selection of item in a menu displayed on the Display Screen 104, or any other conventional user selectable parameter value scheme or mechanism. If the user fails to make a selection, then a default value is used, such as a magnification factor of 1.0.

In 804, the primary and auxiliary images are registered so as to be of the same scale and refer to a same position and orientation in a common reference frame so that corresponding structures and objects in the two images have the same coordinates.

In 805, the primary image is displayed on the Display Screen 104 such as a three-dimensional view of the anatomic structure, in which case, a portion of a two-dimensional slice of the auxiliary image of the anatomic structure may be displayed as an overlay in the lens of the magnifying glass. The portion of the two-dimensional slice in this case is defined by a window area having a central point that has the same position and orientation of as the central point of the lens of the magnifying glass, and an area determined by the magnification factor so that the portion of the two-dimensional slice may be enlarged or reduced so as to fit in the lens of the magnifying glass. Since the position and orientation of the magnifying glass is manipulatable by the positioning device to any position in the three-dimensional space of the Display Screen 104, including those within the volume of the anatomic structure, the two-dimensional slice can correspond to any user selected depth within the anatomic structure. Unlike a physical magnifying glass, its view is not limited to inspecting only the exterior of the anatomic structure. For additional details on 805, see the description below in reference to FIG. 9.

In 806, the method then determines whether the magnifying glass command has been turned off by, for example, the user releasing a "grabbed" image of the magnifying glass, or otherwise switching off the association between the magnifying glass and the pointing device by the use of a conventional switch mechanism of some sort. If it has, then the method ends. On the other hand, if it has not, then the method jumps back to 802 and continues to loop through 802-806 until the magnifying glass command is detected to have been turned off. Note that each time the method loops through 802-806, updated versions, if any, of the primary and auxiliary images are processed along with updated values, if any, for the user selectable magnification factor. Thus, if the method proceeds through the looping in a sufficiently fast manner, the user will not notice any significant delay if the user is turning a dial or knob to adjust the magnification factor while viewing the anatomic structure at a selected position and orientation of the magnifying glass.

FIG. 9 illustrates, as an example, a flow diagram of a method for displaying an auxiliary image view of an anatomic structure at a specified magnification factor as an overlay to a primary image view of the anatomic structure in the lens of a user movable magnifying glass. As previously explained, this method may be used to perform 805 of FIG. 8.

In 901, the current position and orientation of a central point of the lens of the magnifying glass are determined in the three-dimensional space of the Display Screen 104. In 902, a two-dimensional slice of the registered volumetric model of the auxiliary image is taken from the perspective of that position and orientation, and a portion of the two-dimensional slice is taken as defined in an auxiliary view window having a central point preferably at that same position and orientation. The area of the auxiliary view window in this case is inversely proportional to that of the lens according to the current magnification factor for the magnifying glass. In 903, the portion of the two-dimensional slice defined by the auxiliary view window is then enlarged by the magnification factor so that it fits in the lens area of the magnifying glass, and in 904, the primary image of the anatomic structure is displayed on the Display Screen 104 with the enlarged portion of the two-dimensional slice of the auxiliary image overlaid in the lens area of the magnifying glass being displayed on the Display Screen 104.

Figure 11:
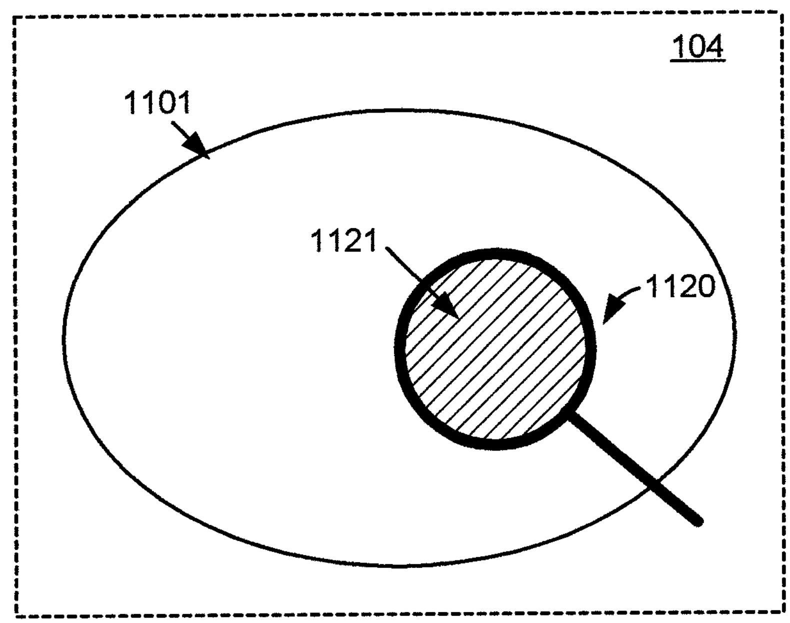
FIG. 11 illustrates a computer display screen with a primary image of an anatomic structure and an overlaid portion of an auxiliary image of the anatomic structure viewed in a magnifying glass lens as displayed by a method utilizing aspects of the present invention.
Figure 10:
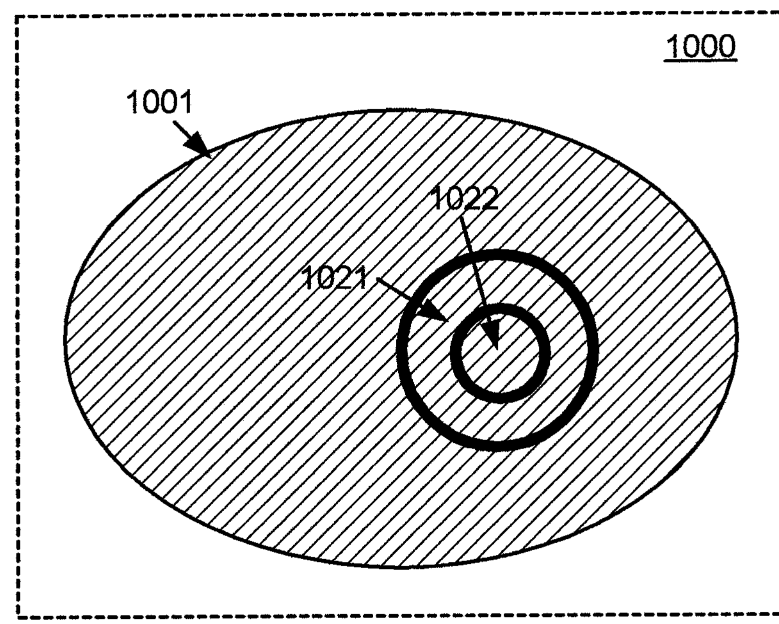
FIG. 10 illustrates an auxiliary image of an anatomic structure and concentric areas of the auxiliary image representing different magnification factors for display on a computer display screen in a magnifying glass by a method utilizing aspects of the present invention.

As a pictorially example of 901-904, in FIGS. 10-11, a two-dimensional slice 1001 of an auxiliary image of an anatomic structure is shown along with two circular windows 1021, 1022 on the two-dimensional slice as illustrated in FIG. 10. Each of the windows 1021, 1022 in this case corresponds in shape to and having a central point equal to that of a lens 1121 of a magnifying glass 1120 which is being displayed along with a primary image of an external view 1101 of the anatomic structure on the Display Screen 104 as illustrated in FIG. 11. In this example, the area of the window 1021 is equal to the area of the lens 1121, so that if the magnification factor was 1.0, then window 1021 would be selected for use in 902. On the other hand, the area of the window 1022 is less than the area of the lens 1121, so that if the magnification factor is greater than 1.0, then the window 1022 may be selected for use in 902. Note that although the lens 1121 of the magnifying glass 1120 is depicted as being circularly shaped, it may also have other common shapes for a magnifying glass, such as a rectangular shape.

Figure 12:
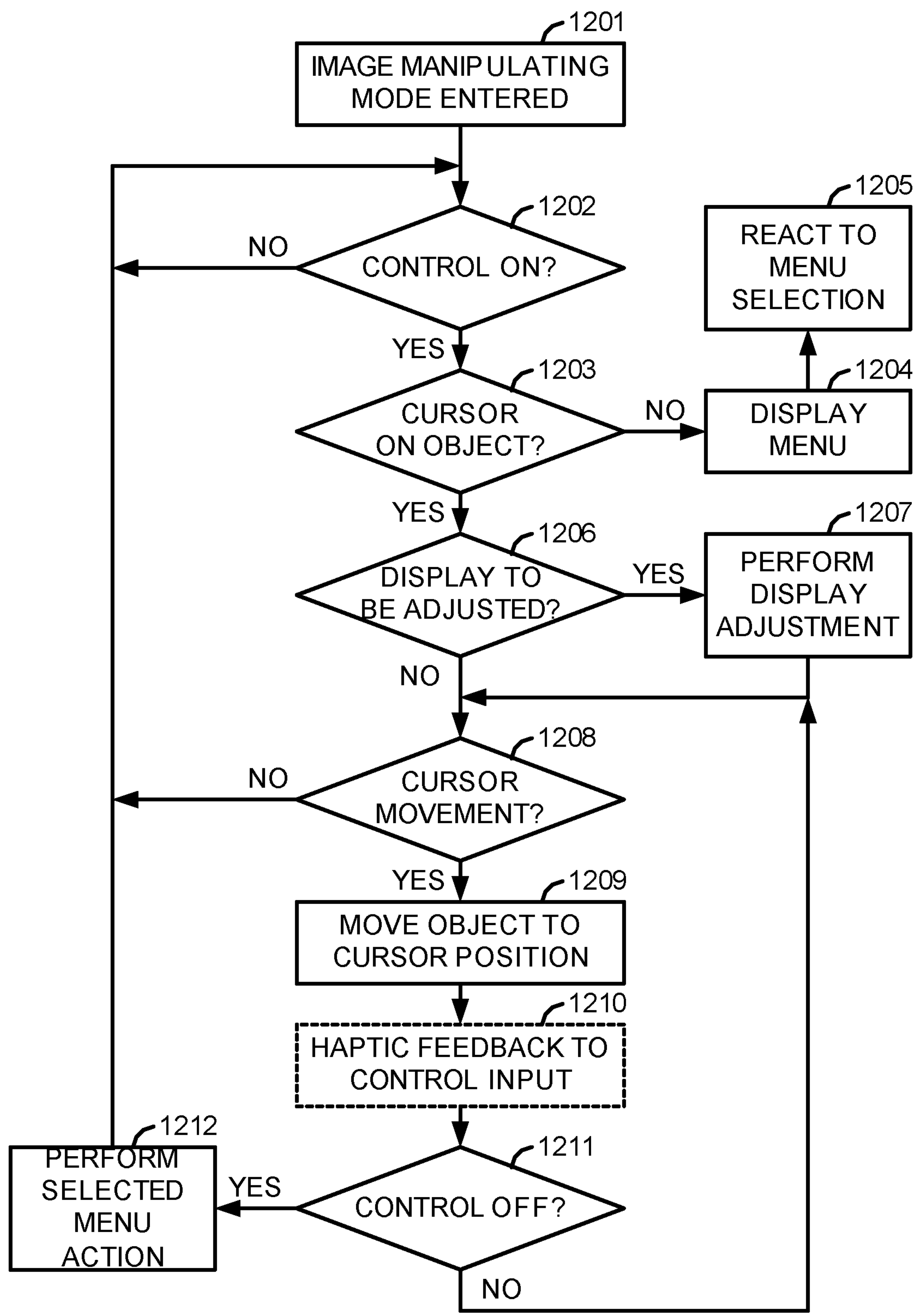
FIG. 12 illustrates a flow diagram of a method performed by a processor in a medical robotic system for manipulating objects displayed on a computer display screen utilizing aspects of the present invention.

FIG. 12 illustrates, as an example, a flow diagram of a method performed by a processor in a medical robotic system for manipulating image objects displayed on a computer display screen of the medical robotic system in response to corresponding manipulation of an associated master input device when the master input device is in an image manipulating mode.

As a preface to the method, the medical robotic system includes an image capturing device to capture images (such as either the Endoscope 140 or the LUS Probe 150); a robotic arm holding the image capturing device (such as the Slave Arm 123 or the Slave Arm 124 respectively holding the Endoscope 140 and the LUS Probe 150); a computer display screen (such as the Display Screen 104); a master input device adapted to be manipulatable by a user in multiple degrees-of-freedom movement (such as the Master Input Device 107 or the Master Input Device 108); and a processor (such as the Auxiliary Controller 242) that is configured to control movement of the image capturing device according to user manipulation of the master input device when the master input device is in an image capturing mode, and control the displaying of images derived from the captured images on the computer display screen according to user manipulation of the master input device when the master input device is in the image manipulating mode.

In 1201, the processor detects that the user has placed the master input device into its image manipulating mode. One way that this may be implemented is using a master clutch mechanism provided in the medical robotic system, which supports disengaging the master input device from its associated robotic arm so that the master input device may be repositioned. When this mode is activated by some mechanism such as the user depressing a button on the master input device, pressing down on a foot pedal, or using voice activation, the associated robotic arm is locked in position, and a cursor (nominally an iconic representation of a hand, e.g. ) is presented to the user on the computer display screen. When the user exits this mode, the cursor is hidden and control of the robotic arm may be resumed after readjusting its position if required.

In 1202, the processor determines whether a control input such as that generated by depressing a button on a conventional mouse has been activated by the user. The control input in this case may be activated by depressing a button provided on the master input device, or it may be activated by some other fashion such as squeezing a gripper or pincher formation provided on the master input device. For additional details on clutching, and gripper or pincher formations on a master input device, see, e.g., commonly owned U.S. Pat. No. 6,659,939 entitled "Cooperative Minimally Invasive Telesurgical System," which has been previously incorporated herein by reference. If the control input is not determined to be "on" (i.e., activated) in 1202, then the processor waits until it either receives an "on" indication or the image manipulating mode is exited.

In 1203, after receiving an indication that the control input is "on", the processor checks to see if the cursor is positioned on (or within a predefined distance to) an object being displayed on the computer display screen. If it is not, then in 1204, the processor causes a menu of user selectable items or actions to be displayed on the computer display screen, and in 1205, the processor receives and reacts to a menu selection made by the user.

Examples of user selectable menu items include: magnifying glass, cut-plane, eraser, and image registration. If the user selects the magnifying glass item, then an image of a magnifying glass is displayed on the computer display screen and the method described in reference to FIG. 8 may be performed by the processor. When the user is finished with the magnifying glass function, then the user may indicate exiting of the function in any conventional manner and the processor returns to 1202.

If the user selects the cut-plane item, then a plane (or rectangular window of fixed or user adjustable size) is displayed on the computer display screen. The master input device may then be associated with the plane so that the user may position and orientate the plane in the three-dimensional space of the computer display screen by manipulating the master input device in the manner of a pointing device. If the plane is maneuvered so as to intersect a volume rendering of an anatomic structure, then it functions as a cut-plane defining a two-dimensional slice of the volume rendering at the intersection. Alternatively, the master input device may be associated with the volume rendering of the anatomic structure, which may then be maneuvered so as to intersect the displayed plane to define the cut-plane. Association of the plane or volume rendering with the pointing device may be performed in substantially the same manner as described in reference to the magnifying glass with respect to 801 of FIG. 8.

The two-dimensional slice may then be viewed either in the plane itself, or in a separate window on the computer display screen such as in a picture-in-picture. The user may further select the cut-plane item additional times to define additional two-dimensional slices of the volume rendering for concurrent viewing in respective planes or picture-in-picture windows on the computer display screen. So as not to clutter the computer display screen with unwanted cut-plane slices, a conventional delete function is provided so that the user may selectively delete any cut-planes and their corresponding slices. When the user is finished with the cut-plane function, then the user may indicate exiting of the function in any conventional manner and the processor returns to 1202.

If the user selects the eraser item, then an eraser is displayed on the computer display screen. The master input device is then associated with the eraser so that the user may position and orientate the eraser in the three-dimensional space of the computer display screen by manipulating the master input device in the manner of a pointing device. Association of the eraser with the pointing device in this case may be performed in substantially the same manner as described in reference to the magnifying glass with respect to 801 of FIG. 8. If the eraser is maneuvered so as to intersect a volume rendering of an anatomic structure, then it functions to either completely or partially erase such rendering wherever it traverses the volume rendering. If partial erasing is selected by the user (or otherwise pre-programmed into the processor), then each time the eraser traverses the volume rendering, less detail of the anatomic structure may be shown. Less detail in this case may refer to the coarseness/fineness of the rendering, or it may refer to the stripping away of layers in the three-dimensional volume rendering. All such characteristics or options of the erasing may be user selected using conventional means. If the user inadvertently erases a portion of the volume rendering, a conventional undo feature is provided to allow the user to undo the erasure. When the user is finished with the erasing function, then the user may indicate exiting of the function in any conventional manner and the processor returns to 1202.

In addition to an eraser function as described above, other spatially localized modifying functions are also contemplated and considered to be within the full scope of the present invention, including selectively sharpening, brightening, or coloring portions of a displayed image to enhance its visibility in, or otherwise highlight, a selected area. Each such spatially localized modifying function may be performed using substantially the same method described above in reference to the eraser function.

If the user selects the image registration item, then the processor records such selection for future action as described below in reference to 1212 before jumping back to process 1202 again. Image registration in this case typically involves manually registering an auxiliary image of an object such as an anatomic structure with a corresponding primary image of the object.

As an alternative to the above described menu approach, icons respectively indicating each of the selectable items as described above may be displayed on the computer display screen upon entering image manipulating mode and selected by the user clicking on them, after which, the processor proceeds to perform as described above in reference to selection of their corresponding menu items.

Now continuing with the method described in reference to FIG. 12, after receiving an indication that the control input is on in 1201 and determining that the cursor is positioned on or near an object (not an icon) being displayed on the computer display screen in 1202, the processor preferably changes the cursor from an iconic representation of a hand, for example, to that of a grasping hand to indicate that the object has been "grabbed" and is ready to be moved or "dragged" to another position and/or orientation in the three-dimensional space of the computer display screen through user manipulation of the master input device.

In 1206, the processor then determines whether the user has indicated that a display parameter of the selected object is to be adjusted, and if the user has so indicated, in 1207, the processor performs the display adjustment. As an example, a dial on the master input device may be turned by the user to indicate both that a display adjustment for a display parameter associated with dial is to be adjusted according to the amount of rotation of the dial on the selected object. Alternatively, if the master input device is equipped with a gripper, the gripper may be rotated so as to function as a dial. Examples of display parameters that may be adjusted in this manner include: brightness, contrast, color, and level of detail (e.g., mesh coarseness/fineness, or voxel size and/or opaqueness) of the selected object being displayed on the computer display screen.

The processor then proceeds to 1208 to determine whether the cursor has moved since "grabbing" the selected object after an affirmative determination in 1203. If it has not moved, then the processor jumps back to 1202 since the user may only have wanted to adjust a display parameter of a selected object at this time. On the other hand, if the cursor has moved since "grabbing" the selected object, then in 1209, the processor moves the selected object to the new cursor position. Since the cursor operates in the three-dimensional space of the computer display screen, when it moves "into" the display screen, it may indicate such movement by, for example, getting progressively smaller in size. Where the three-dimensional nature of the computer display screen is achieved through the use of right and left two-dimensional views of the object with disparities of common points between the two views indicating depth values, decreasing of the depth values for images of the cursor in the right and left views indicates that the cursor is moving "into" the display screen.

Optionally, in 1210, haptic feedback may be provided back to the master input device so that the user may sense reflected forces while the "grabbed" object is being moved in 1209. As an example, user interactions with the object may be reflected haptically back to the user by associating a virtual mass and inertial properties with the object so that the user feels a reflected force when coming into contact with the object or when translating or rotating the object as it is accelerated/decelerated. The haptic feedback performed in this 1210 may only be performed for some types of objects and not for others, or it may take effect only in certain circumstances. Use of such haptic feedback may also be applied to the movement of the magnifying glass and/or the plane used for defining cut-planes as described above. In such cases, however, the haptic feedback may be restricted to only occurring after the magnifying glass or the plane enters into an anatomic structure of interest.

In 1211, the processor determines whether the control input is still in an "on" state. If the control is still "on", then the processor jumps back to 1208 to track and respond to cursor movement. On the other hand, if the control has been turned off by, for example, the user releasing a button that was initially depressed to indicate that control was turned "on", then in 1212, the processor performs a selected menu action.

For example, if the image registration item had been selected by the user in response to the processor displaying the menu in 1204 (or alternatively, the user clicking an icon indicating that item), then the object that has been moved is registered with another image of the object that is now aligned with and is being displayed on the computer display screen at the time so that they have the same coordinate and orientation values in a common reference frame such as that of the computer display screen. This feature facilitates, for example, manual registration of an auxiliary image of an anatomic structure (such as obtained using the LUS Probe 150) with a primary image of the anatomic structure (such as obtained using the Endoscope 140). After the initial registration, changes to the position and/or orientation of the corresponding object in the primary image may be mirrored so as to cause corresponding changes to the selected object in the auxiliary image so as to maintain its relative position/orientation with respect to the primary image. When the user is finished with the image registration function, then the processor returns to 1202.

Although the various aspects of the present invention have been described with respect to a preferred embodiment, it will be understood that the invention is entitled to full protection within the full scope of the appended claims.

What is claimed is:

1. A medical system comprising:
a stereo display;
an input device; and
a processor configured to:
generate a three-dimensional image of an anatomical object from scanned images of the object;
cause the three-dimensional image of the anatomical object and a two-dimensional window to be displayed on the stereo display;
cause a position and an orientation of the two-dimensional window relative to the three-dimensional image of the anatomical object to be changed on the stereo display, according to manipulation of the input device after associating the two-dimensional window with the input device;
define a cut-plane by an intersection of the two-dimensional window with the three-dimensional image of the anatomical object so as to indicate a two-dimensional slice of the three-dimensional image of the anatomical object; and
cause the two-dimensional slice of the three-dimensional image of the anatomical object to be displayed on the stereo display, wherein an orientation of the displayed two-dimensional slice of the three-dimensional image of the anatomical object is different than an orientation of the cut-plane with the three-dimensional image of the anatomical object.

2. The medical system according to claim 1, wherein the input device is configured so as to be manipulatable in multiple degrees of freedom so that the input device operates as a three-dimensional mouse.

3. The medical system according to claim 1, wherein the processor is further configured to:
associate the input device with the two-dimensional window after a user activates a control input while a cursor associated with the input device is being displayed on the two-dimensional window on the stereo display.

4. The medical system according to claim 1, wherein the processor is further configured to:
provide haptic feedback to the input device while causing the position and the orientation of the two-dimensional window to be changed on the stereo display.

5. The medical system according to claim 4, wherein the haptic feedback is provided by associating a virtual mass and inertial properties to the two-dimensional window so that a user manipulating the input device would feel a reflected force on the input device while the position and the orientation of the two-dimensional window is being changed in response to the user manipulating the input device.

6. The medical system according to claim 1, wherein the two-dimensional slice is displayed in the two-dimensional window on the stereo display.

7. The medical system according to claim 1, wherein the two-dimensional slice is displayed in a picture-in-picture window on the stereo display.

8. The medical system according to claim 1, wherein the processor is further configured to:
display a second two-dimensional window on the stereo display,
cause a position and an orientation of the second two-dimensional window relative to the three-dimensional image of the anatomical object to be changed on the stereo display, according to manipulation of the input device after associating the second two-dimensional window with the input device;
define a cut-plane by an intersection of the second two-dimensional window with the three-dimensional image of the anatomical object so as to indicate a second two-dimensional slice of the three-dimensional image of the anatomical object; and cause the second two-dimensional slice of the three-dimensional image of the anatomical object to be displayed on the stereo display.

9. The medical system according to claim 8, wherein the two-dimensional slice and the second two-dimensional image slice are displayed in corresponding picture-in-picture windows on the stereo display.

10. The medical system according to claim 1, wherein the processor is further configured to:

display the two-dimensional window on the stereo display in response to user selection of an item included in a menu being displayed on the stereo display.

11. The medical system according to claim 1, wherein the processor is further configured to:

display the two-dimensional window on the stereo display in response to user selection of an icon being displayed on the stereo display.

12. The medical system according to claim 11, wherein the icon is displayed in a periphery area of the stereo display, and wherein the processor is further configured to:

interpret user mouse-type actions of clicking on the icon and dragging the icon away from the periphery area as a user selection of the icon.

13. The medical system according to claim 12, wherein the scanned images of the anatomical object comprise two-dimensional ultrasound slices captured by an ultrasound probe.

14. A method comprising:

a processor generating a three-dimensional image of an anatomical object from scanned images of the object;

the processor causing the three-dimensional image of the anatomical object and a two-dimensional window to be displayed on a stereo display;

the processor changing a position and an orientation of the two-dimensional window relative to the three-dimensional image of the anatomical object on the stereo display, according to manipulation of an input device after associating the two-dimensional window with the input device;

the processor defining a cut-plane by an intersection of the two-dimensional window with the three-dimensional image of the anatomical object so as to indicate a two-dimensional slice of the three-dimensional image of the anatomical object; and the processor causing the two-dimensional slice of the three-dimensional image of the anatomical object to be displayed on the stereo display, wherein an orientation of the displayed two-dimensional slice of the three-dimensional image of the anatomical object is different than an orientation of the cut-plane with the three-dimensional image of the anatomical object.

15. The method according to claim 14, further comprising:

the processor associating the input device with the two-dimensional window after a user activates a control input while a cursor associated with the input device is being displayed on the two-dimensional window on the stereo display.

16. The method according to claim 14, further comprising:

the processor providing haptic feedback to the input device while changing the position and the orientation of the two-dimensional window on the stereo display.

17. The method according to claim 14, wherein the processor causes the two-dimensional slice of the three-dimensional image of the anatomical object to be displayed on the stereo display by causing the two-dimensional slice to be displayed in the two-dimensional window on the stereo display.

18. The method according to claim 14, wherein the processor causes the two-dimensional slice of the three-dimensional image of the anatomical object to be displayed on the stereo display by causing the two-dimensional slice to be displayed in a picture-in-picture window on the stereo display.

19. The method according to claim 14, wherein the processor causes the two-dimensional window to be displayed on the stereo display in response to user selection of an item included in a menu being displayed on the stereo display.

20. The method according to claim 14, wherein the processor causes the two-dimensional window to be displayed on the stereo display in response to user selection of an icon being displayed on the stereo display.

* * * * *